United States Patent
Pei

(10) Patent No.: US 10,092,759 B2
(45) Date of Patent: Oct. 9, 2018

(54) SELF-LEARNING METHOD AND DEVICE FOR MANAGING INTRACARDIAC CYCLE EXTENSION

(71) Applicant: PACESETTER, INC., Sylmar, CA (US)

(72) Inventor: Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 283 days.

(21) Appl. No.: 14/918,390

(22) Filed: Oct. 20, 2015

(65) Prior Publication Data
US 2017/0106191 A1 Apr. 20, 2017

(51) Int. Cl.
A61N 1/362 (2006.01)
A61N 1/02 (2006.01)
A61N 1/368 (2006.01)

(52) U.S. Cl.
CPC ........... *A61N 1/3622* (2013.01); *A61N 1/025* (2013.01); *A61N 1/3684* (2013.01)

(58) Field of Classification Search
CPC ..... A61N 1/3622; A61N 1/3684; A61N 1/025
See application file for complete search history.

(56) References Cited

U.S. PATENT DOCUMENTS

2004/0024421 A1* 2/2004 Ideker ............... A61N 1/368
607/9

* cited by examiner

*Primary Examiner* — Alyssa M Alter

(57) ABSTRACT

An implantable medical device is provided that comprises a pulse generator circuit that times delivery of ventricular pacing pulses based on a base intracardiac interval (ICI). A processor is provided that has memory storing program instructions and storing atrial and ventricular events over multiple cardiac cycles and that is responsive to execution of the program instructions. The processor adjusts the base ICI by an ICI adjustment, during one or more of the multiple cardiac cycles, to promote intrinsic heart activity. The processor further counts a number of the cardiac cycles in which the ICI adjustments occurred in conjunction with arrhythmias to identify an excessive adjustment count and modifies the ICI adjustment to utilize a new ICI adjustment based on the excessive adjustment count.

20 Claims, 10 Drawing Sheets

SELF-LEARNING METHOD AND DEVICE FOR MANAGING INTRACARDIAC CYCLE EXTENSION

BACKGROUND

Embodiments of the present disclosure generally relate to methods and devices for managing intracardiac cycle extension through self-learning.

Numerous implantable medical devices exist today that implement a variety of detection schemes and therapies to address various arrhythmias while seeking to promote intrinsic cardiac behavior. An example of an operation mode for a pacemaker represents a DDD pacing mode. In the DDD pacing mode, among other things, a ventricular sensing channel waits for a conducted beat until a programmed atrial ventricular (AV) delay times out. When the AV delay times out without sensing an intrinsic event, the pacemaker delivers a ventricular pacing pulse. When the AV delay is programmed to be relatively short, the pacemaker may deliver ventricular pacing pulses during a relatively large percentage of the cardiac events. The option exists for a physician to program longer AV delays in an attempt to increase the frequency of intrinsic conduction. However, when the AV delay is unduly lengthened, the longer AV delays may introduce complications such as non-physiologic intervals between intrinsic atrial and ventricular events, pacemaker-mediated tachycardia, and artificially limited maximum tracking rates. Consequently, conventional approaches experienced difficulties in managing AV delays to promote conduction without introducing other complications. The foregoing difficulties are also experienced by implantable cardioverter defibrillators (ICDs).

The settings of many sophisticated algorithms in contemporary implantable medical devices that manage a patient's rhythms/arrhythmias can only be modified during office visits/follow-ups. In general, algorithms that manage the patient's rhythms/arrhythmias have no capability for self-adjustment. Consequently, undesired cardiac rhythms may result from the algorithm's behavior due to non-optimized parameters. Examples of algorithms include the ventricular intrinsic preference (VIP) algorithm, managed ventricular pacing (MVP), atrial overdrive pacing and rate adaptive refractory management. The MVP algorithm and VIP algorithm, both seek to minimize ventricular pacing. However, for some patients, the MVP may induce certain nonphysiologic behavior that is difficult to diagnose due to lack of diagnostic information. Pacemaker-mediated tachycardia may result in some patients when algorithms, such as the VIP or MVP algorithms, modified the intracardiac cycle interval (e.g. the AV interval) in an effort to promote intrinsic ventricular activity and to minimize right ventricular pacing.

Given the complexity of an implantable medical device (IMD) today, difficulties have been experienced in attempting to program the IMD to the optimal settings for a patient during implant or during a single follow-up visit. Further, sometimes the IMD may be programmed non-optimally or inappropriately, and may operate in this manner for relatively long periods of time between scheduled follow up visits (which may be from three to six months). Moreover, even when the parameters are set appropriately during implant or follow up, over time, the programmed parameters may become non-optimal when the disease progresses or the patient's underlying rhythm changes. Non-optimal or inappropriate programming may cause patient discomfort and/or may lead to adverse effects.

A need remains for improved methods and devices to manage modification to base intracardiac delay intervals utilized by IMDs when attempting to promote intrinsic physiologic behavior.

SUMMARY

In accordance with embodiments, an implantable medical device is provided that comprises a pulse generator circuit that times delivery of ventricular pacing pulses based on a base intracardiac interval (ICI). A processor is coupled to memory storing program instructions and storing atrial and ventricular events over multiple cardiac cycles. The processor is responsive to execution of the program instructions. The processor adjusts the base ICI by an ICI adjustment, during one or more of the multiple cardiac cycles, to promote intrinsic heart activity. The processor further counts a number of the cardiac cycles in which the ICI adjustments occurred in conjunction with arrhythmias to identify an excessive adjustment count and modifies the ICI adjustment to utilize a new ICI adjustment based on the excessive adjustment count.

Optionally, the base ICI corresponds to at least one of an AV interval or a PVARP interval and the ICI adjustment corresponds to at least one of an AV extension or a rate adaptive refractory reduction. The adjust operation changes the base ICI utilizing different ICI adjustments during different corresponding cardiac cycles within the multiple cardiac cycles.

Optionally, the processor further identifies the arrhythmias that are induced by extending the base ICI by the ICI adjustment in connection with AV extension. The processor identifies the arrhythmias that are induced by reducing the base ICI by the ICI adjustment in connection with rate adaptive refractory adjustment. The processor measures intervals between ventricular and atrial events and identifies a select level of change within the intervals between the ventricular and atrial events associated with an arrhythmia.

Optionally, the processor confirms when pacemaker-mediated-tachycardia (PMTs) occur and increments the excessive adjustment count for at least a portion of the PMTs. The modify operation includes reducing the ICI adjustment by a predetermined amount and includes changing the ICI adjustment to correspond to a prior ICI adjustment. The base ICI corresponds to at least one of a base AV interval or a post ventricular atrial refractory period (PVARP) interval.

In accordance with embodiments, a method is provided for managing modifications to intracardiac intervals, that comprises timing a pulse generator circuit to deliver ventricular pacing pulses based on a base intracardiac interval (ICI), storing atrial and ventricular events over multiple cardiac cycles and adjusting the base ICI by an ICI adjustment, during one or more of the multiple cardiac cycles, to promote intrinsic heart activity. The method further comprises counting a number of the cardiac cycles in which the ICI adjustments occurred in conjunction with arrhythmias to identify an excessive adjustment count and modifying the ICI adjustment to utilize a new ICI adjustment based on the excessive adjustment count.

Optionally, the base ICI corresponds to at least one of an AV interval or a rate adaptive PVARP interval and the ICI adjustment corresponds to at least one of an AV extension or a rate adaptive refractory reduction. The adjusting operation changes the base ICI utilizing different ICI adjustments during different corresponding cardiac cycles within the multiple cardiac cycles. The method further comprises identifying the arrhythmias that are induced by extending the base ICI by the ICI adjustment in connection with AV extension and identifying the arrhythmias that are induced by reducing the base ICI by the ICI adjustment in connection with rate adaptive refractory reduction.

Optionally, the method further comprises measuring intervals between ventricular and atrial events and identifying a select level of change within the intervals between the ventricular and atrial events. The modifying operation includes reducing the ICI adjustment by a predetermined amount. The modifying operation includes changing the ICI adjustment to correspond to a prior ICI adjustment. The base ICI corresponds to at least one of a base AV interval or a post ventricular atrial refractory period (PVARP) interval. The method further comprises delivering a corrective therapy from the pulse generator circuit.

DETAILED DESCRIPTION

Figure 1A:
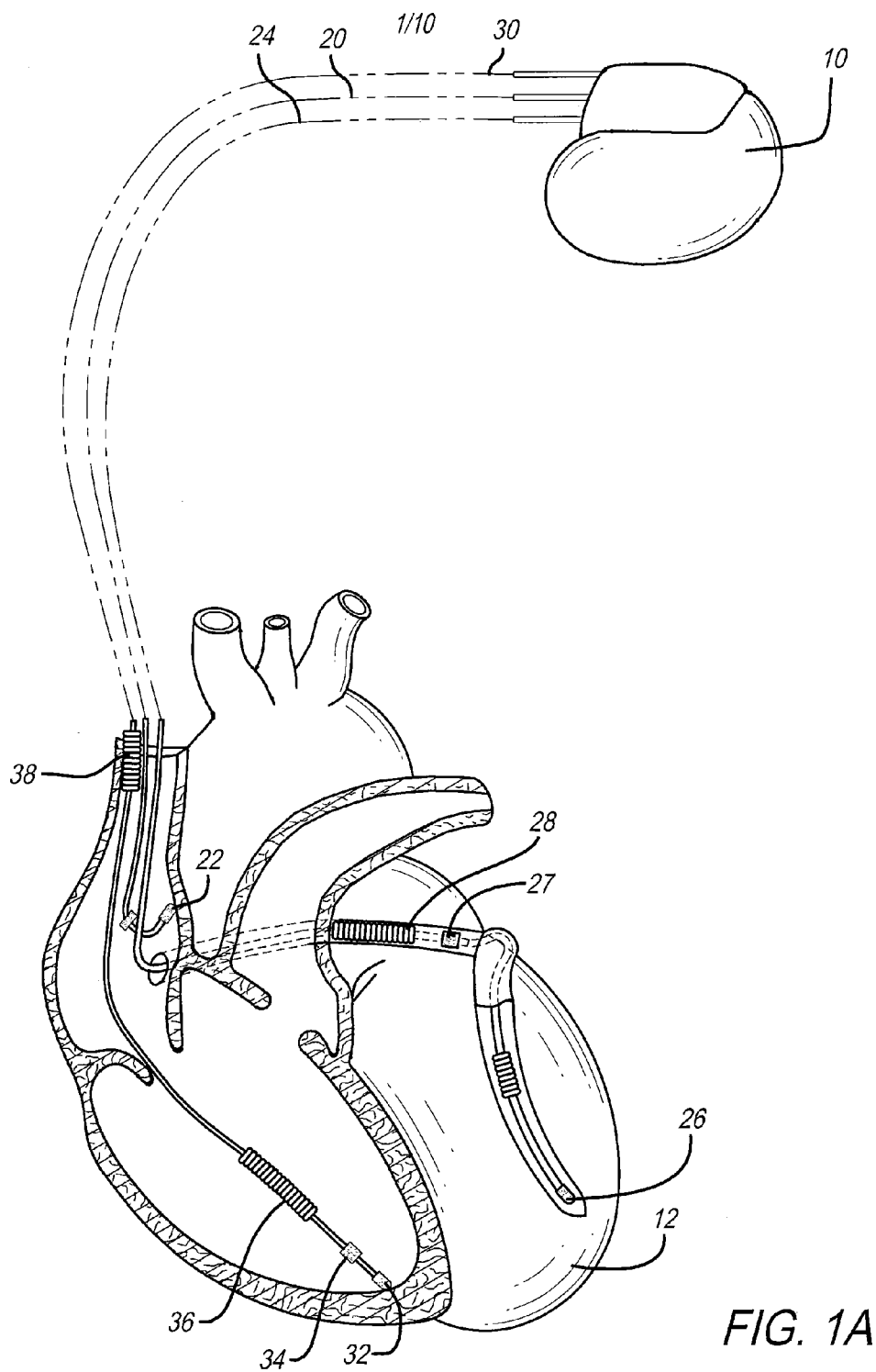
FIG. 1A, illustrates a stimulation device in electrical communication with a patient's heart by way of three leads suitable for delivering multi-chamber stimulation and shock therapy in accordance with embodiments herein.

It will be readily understood that the components of the embodiments as generally described and illustrated in the FIGS. herein, may be arranged and designed in a wide variety of different configurations in addition to the described example embodiments. Thus, the following more detailed description of the example embodiments, as represented in the FIGS., is not intended to limit the scope of the embodiments, as claimed, but is merely representative of example embodiments.

For convenience, the following terminology is abbreviated throughout the present application as denoted in (parenthesis):
A. trial paced event (P);
B. atrial sensed event (A);
C. ventricular paced event (V);
D. ventricular event (R);
E. implantable medical device (IMD);
F. ventricular paced-atrial paced interval (V-P interval);
G. ventricular sensed-atrial paced interval (R-P interval);
H. pacemaker mediated tachycardia (PMT);
I. post ventricular atrial refractory period (PVARP);
J. intracardiac interval (ICI);
K. rate adaptive refractory (RAR).

Embodiments herein address the aforementioned issues/disadvantages of IMDs by utilizing self-learning mechanisms. By way of example, the self-learning mechanism collects diagnostics of interest and determines an appropriateness of a preprogrammed parameter that modifies a base therapy parameter set. Based on the appropriateness of the preprogrammed parameter, embodiments herein adjust/fine-tune the parameter accordingly, to reduce inappropriate therapy and to enhance therapy efficacy. In accordance with embodiments herein, methods and devices are described that, among other things, improve the quality of life of the patients, reduce the risks associated with the non-optimal/inappropriate programmed settings, and provide valuable diagnostics for evaluating the efficacy and appropriateness of therapy for physician and for clinical studies.

In certain modes of operation, traditional IMDs seek to promote intrinsic AV conduction using intracardiac interval (ICI) adjustment algorithms such as VIP and MVP. When using the VIP, MVP or other AV conduction promotion algorithms, the IMD adjusts the ICI, such as by extending the AV/PV delay. As another example, the IMD may adjust the IDI by switching the mode to a non-ventricular pacing mode. However, ICI adjustment raises the potential that an arrhythmia (e.g. a PMT) may be induced because the increase in the AV interval may enable the atrium to become susceptible to retrograde conduction. The atrium may become susceptible to retrograde conduction when the AV node and atrial tissue recover sufficiently to allow retrograde conduction.

Embodiments herein provide methods and devices that seek to address root causes of the foregoing issues, that is the extension of the AV/PV interval or when no V-pacing occurs for an excessive period of time. The methods and devices herein count the number of VIP time extensions (or in MVP, switching to a non-V-pacing mode) and the number of PMT events that follow the extension/switch. After extension of the AV/PV or switching to non-ventricular pacing mode, the methods and devices herein measure the V-P and/or R-P intervals. If there is a sudden change in the V-P or R-P interval, the methods and devices herein further confirm the PMT. If the PMT is further confirmed, a counter that tracks a number of inappropriate extensions is updated for the corresponding specific condition. If the counter exceeds a pre-defined threshold, the methods and devices herein modify the ICI adjustment, such as to reduce the VIP extension or adjust the non-ventricular pacing mode. The counter(s) facilitate a self-learning process that tracks the number of PMTS (or other arrhythmias) that occurs in conjunction with ICI adjustments.

By reducing the VIP extension, adjusting the non-ventricular pacing mode or other ICI adjustment, the methods and devices reduce/eliminate the cause of the retrograde conduction during future cardiac cycles. Further, based on the counter history, future ICI adjustment may be rendered dependent on activity level, circadian information and heart rate where appropriate. The methods and devices may also provide a T-retrograde for quick PMT detection so that the methods and devices respond quickly to similar arrhythmias, and PVARP value setting references.

In accordance with embodiments herein, methods and devices provide self-learning processes that limit rate adaptive refractory self adjustment of an IMD relative to intrinsic non-physiologic intracardiac behavior. A heart may exhibit non-physiologic intracardiac behavior wherein, non-physiologic intrinsic events occur absent interruption by (or in response to) paced events. An example of a non-physiologic intrinsic event represents a retrograde event in which retrograde conduction occurs from one or both ventricles to one or both atrium. Retrograde events may appear as atrial intrinsic events. In certain implementations, an IMD engages a rate adaptive algorithm that shortens the refractory delay as the pacing rate increases. Without the self-learning mechanisms herein, the IMD may overly shorten the refractory period such that the IMD begins to track the retrograde events in the atrium. Without the self-learning mechanisms herein, when the IMD delivers paced ventricular events following each atrial retrograde event, a pacemaker mediated tachycardia (PMT) may result.

In accordance with self-learning processes described herein, methods and devices determine when the refractory delay is overly shortened, thereby enabling retrograde conduction to reach an atrium before delivery of a paced event in the atrium. When the refractory delay is unduly shortened, the retrograde events were hidden. As a consequence, conventional IMDs will track the retrograde conduction and cause a PMT. When used in connection with refractory shortening, embodiments here count the number of Shortening and the PMT events that follow the shortening. After shortening of the PVARP, the methods and devices measure the V-P and/or R-P intervals. If there is a sudden change of V-P or R-P interval, further confirmation of the PMT is be performed. If the PMT is confirmed, the counter for the inappropriate shortening is updated for this specific condition. If the counter exceeds a pre-defined threshold, the methods and devices reduce the degree of PVARP shortening. This would reduce/eliminate the cause of the retrograde conduction in the future. With the learned history, the future PVARP shortening will be then dependent on activity level, circadian information and heart rate where appropriate.

As shown in FIG. 1A, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrium.

To sense left atrial and ventricular cardiac signals and to provide left chamber pacing therapy, the medical or stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive left atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricle so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 1B:
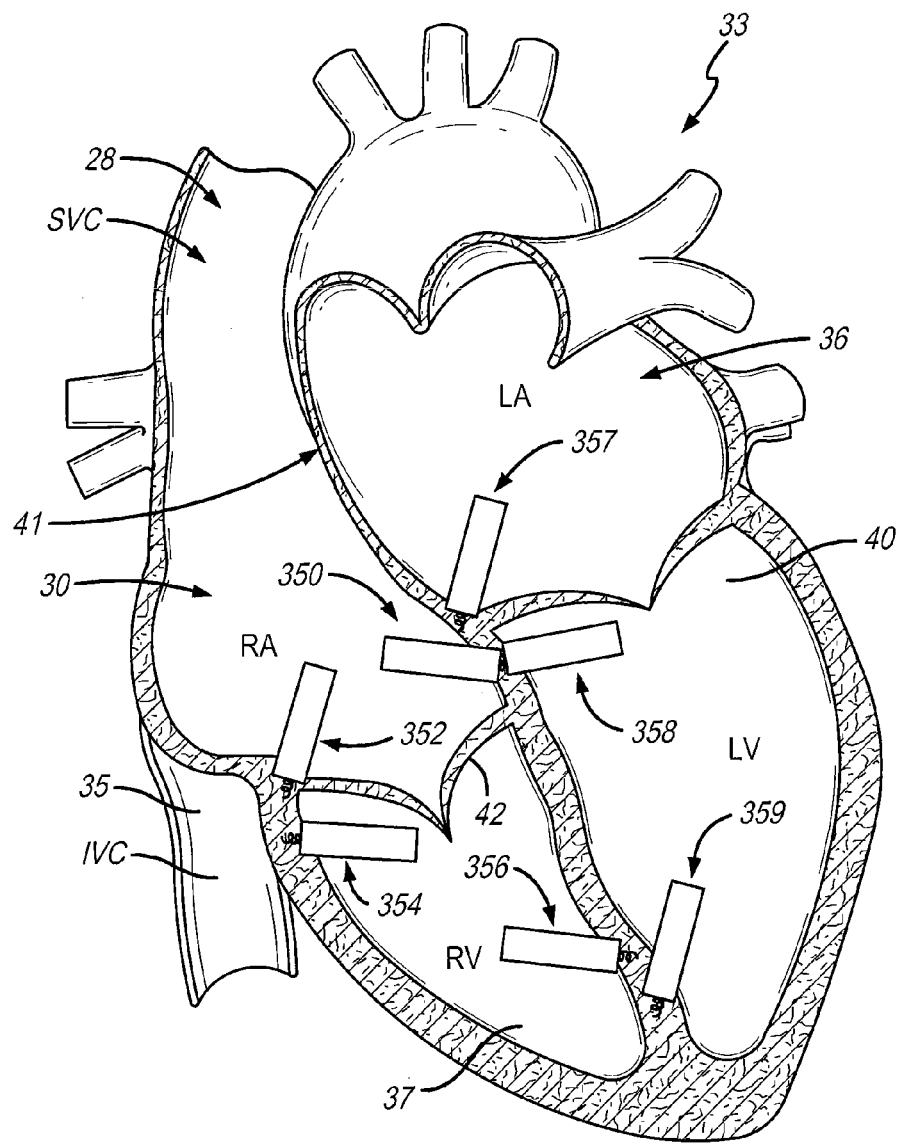
FIG. 1B illustrates various leadless implantable medical devices that may be utilized in accordance with embodiments herein.

FIG. 1B illustrates various leadless implantable medical devices (LIMDs) that may be utilized in accordance with embodiments herein. One or more of the LIMDs 350-356 may be used alone or in combination. For example, the LIMD may be implanted in the RA and capable of pacing the RV. Optionally, the LIMD may also be located in other locations. At 350, the LIMD is capable of HISian or para-HISian pacing to produce excitation of the RV and LV. When the LIMD is implanted at 352, the LIMD is able to provide RA/RV sensing and pacing from the RA. When the LIMD is implanted at 354, the LIMD is able to provide RA/RV sensing and pacing from the RV. When the LIMD is implanted at 356, the LIMD is able to provide RV/LV sensing and pacing from the RV. The LIMDs 357, 358, 359 afford LA/RA pacing and sensing, LV/RA pacing and sensing, and LV/RV pacing and sensing, respectively.

FIG. 1B illustrates various leadless implantable medical devices (LIMDs) that may be utilized in accordance with embodiments herein. One or more of the LIMDs 350-356 may be used alone or in combination. For example, the LIMD may be implanted in the RA and capable of pacing the RV. Optionally, the LIMD may also be located in other locations. At 350, the LIMD is capable of HISian or para-HISian pacing to produce excitation of the RV and LV. When the LIMD is implanted at 352, the LIMD is able to provide RA/RV sensing and pacing from the RA. When the LIMD is implanted at 354, the LIMD is able to provide RA/RV sensing and pacing from the RV. When the LIMD is implanted at 356, the LIMD is able to provide RV/LV sensing and pacing from the RV. The LIMDs 357, 358, 359 afford LA/RA pacing and sensing, LV/RA pacing and sensing, and LV/RV pacing and sensing, respectively.

Figure 2:
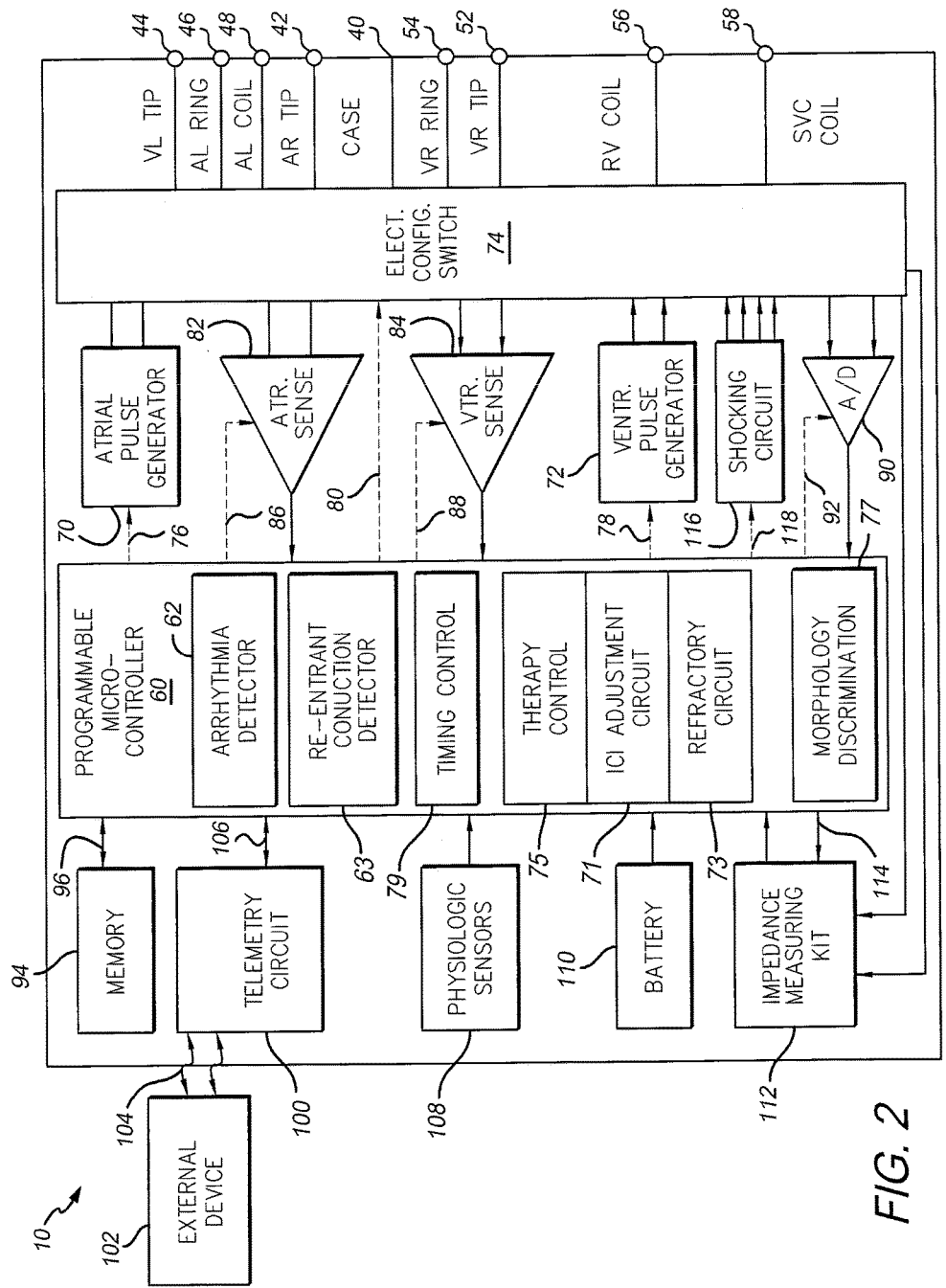
FIG. 2 illustrates a simplified block diagram is shown a multi-chamber implantable stimulation device in accordance with embodiments herein.

As illustrated in FIG. 2, a simplified block diagram is shown a multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The blocks illustrated in FIG. 2 represent functional blocks which may be implemented in hardware, discrete logic, firmware, software, in or with a single CPU, multiple CPUs, field programmable gate arrays and the like. The terms "circuit" and "module" are used throughout interchangeably to refer to functional blocks.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

A programmable microcontroller or processor 60 is provided which controls the various modes of stimulation therapy. The microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The processor is responsive to execution of the program instructions. The processor adjusts the base ICI by an ICI adjustment, during one or more of the multiple cardiac cycles, to promote intrinsic heart activity. The processor further counts a number of the cardiac cycles in which the ICI adjustments occurred in conjunction with arrhythmias to identify an excessive adjustment count and modifies the ICI adjustment to utilize a new ICI adjustment based on the excessive adjustment count. The adjust operation changes the base ICI utilizing different ICI adjustments during different corresponding cardiac cycles within the multiple cardiac cycles.

Optionally, the processor further identifies the arrhythmias that are induced by extending the base ICI by the ICI adjustment in connection with AV extension. The processor identifies the arrhythmias that are induced by reducing the base ICI by the ICI adjustment in connection with rate adaptive refractory reduction. The processor measures intervals between ventricular and atrial events and identifies a select level of change within the intervals between the ventricular and atrial events.

Optionally, the processor confirms when pacemaker-mediated-tachycardia (PMTs) occur and increments the excessive adjustment count for at least a portion of the PMTs. The modify operation includes reducing the ICI adjustment by a predetermined amount and includes changing the ICI adjustment to correspond to a prior ICI adjustment. The base ICI corresponds to at least one of a base AV interval or a post ventricular atrial refractory period (PVARP) interval.

As shown in FIG. 2, an atrial pulse generator circuit 70 and a ventricular pulse generator circuit 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generator circuit, 70 and 72, may include dedicated, independent pulse generators, multiplexed pulse generators, or shared pulse generators. The pulse generator circuit, 70 and 72, are controlled by the microcontroller 60 via appropriate control signals, 76 and 78, respectively, to trigger or inhibit the stimulation pulses. The pulse generator circuits 70 and 72 time delivery of ventricular pacing pulses based on a base intracardiac interval (ICI). The base ICI corresponds to at least one of an AV interval or a PVARP interval and the ICI adjustment corresponds to at least one of an AV extension or a rate adaptive refractory reduction.

The microcontroller 60 further includes timing control circuitry 79 which is used to control the timing of such stimulation pulses (e.g., pacing rate, atrio-ventricular (AV) interval or delay, ventricular-atrio (VA) interval or delay, atrial interconduction (A-A) delay, or ventricular interconduction (V-V) delay, etc.) as well as to keep track of the timing of blanking intervals, noise detection windows, evoked response windows, alert intervals, marker channel timing, etc., which is well known in the art. The microcontroller 60 also includes a refractory circuit 73. The refractory circuit 73 times refractory periods, including post ventricular atrial refractory periods (PVARP) as described subsequently.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

An arrhythmia detector 62 utilizes the atrial and ventricular sensing circuits, 82 and 84, to sense cardiac signals to determine whether a rhythm is physiologic or non-physiologic/pathologic. The arrhythmia detector 62 detects PMTs and other arrhythmias. As used herein "sensing" is reserved for the noting of an electrical signal, and "detection" is the processing of these sensed sequential signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

A reentrant conduction detector 63 seeks to identify intrinsic reentrant tachycardia involving the atria that might otherwise continue undeclared due, in part, to the occurrence of retrograde P waves during an extended PVARP interval. The reentrant conduction detector 63 identifies an intrinsic reentrant tachycardia based on several parameters, such as intrinsic P waves occurring during the extended AV interval, the PR interval, the RP interval and the R to R interval. For example, the reentrant conduction detector 63 may analyze a series of intrinsic R waves over N cardiac cycles and determine whether the R to R interval corresponds to a heart rate above a rate threshold. The rate threshold may be programmable and/or may be automatically adjusted by the device 10. When the reentrant conduction detector 63 identifies a retrograde P wave, it also searches for an intrinsic QRS complex with stable (e.g., repeating) RP and PR intervals that are indicative of reentrant tachycardia.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. Optionally, other leads with multiple electrodes may be added to the system, to further improve the diagnosis and characterization of the tachyarrhythmia.

Advantageously, the data acquisition system 90 may be coupled to the microcontroller, or other detection circuitry for detecting an evoked response from the heart 12 in response to an applied stimulus, thereby aiding in the detection of "capture". Capture occurs when an electrical stimulus applied to the heart is of sufficient energy to depolarize the cardiac tissue. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, AV interval, AV extension, PVARP interval, PVARP extension, RAR reduction, PR threshold, RP threshold, R to R threshold, rate threshold, electrode polarity, rate, sensitivity, automatic features, arrhythmia detection criteria, and the amplitude, waveshape and vector of each shocking pulse to be delivered to the patient's heart 12 within each respective therapy. The memory 94 may also store the number of corrective therapies to be delivered in successive cardiac cycles to attempt to correct an intrinsic reentrant tachycardia. The memory 94 stores program instructions and atrial and ventricular events over multiple cardiac cycles.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 is capable of operating at low current drains for long periods of time, and then be capable of providing high-current pulses (for capacitor charging) when the patient requires a shock pulse. For example, the device 10 may employ a power source comprised or one or more lithium salts, for example lithium/silver vanadium pentoxide, or other battery technologies known in the art.

Optionally, the device 10 may have an impedance measuring circuit 112 which is enabled by the microcontroller 60 via a control signal 114. The impedance measuring circuit 120 may perform lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 may be omitted.

In the case where the stimulation device 10 is intended to operate as an implantable cardioverter/defibrillator (ICD) device, it detects occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 5 joules), moderate (6 to 15 joules), or high energy (16 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level and/or synchronized with an R-wave and/or pertaining to the treatment of tachycardia. Defibrillation shocks are generally of moderate to high energy level, i.e., corresponding to outputs in the range of 16-40 joules. Although external ICDs deliver the shock asynchronously (since R-waves may be too disorganized and small) in the setting of ventricular fibrillation, the implantable devices still synchronize with a ventricular depolarization signal as fibrillatory signals as recorded from inside the heart may be very discrete.

Accordingly, the microcontroller 60 is capable of controlling the delivery of the shocking pulses of various energy levels depending on the detected rate and identification of the rhythm by the implanted ICD.

The device 10 further includes an ICI adjustment circuit 71. The ICI adjustment circuit 71 initiates an ICI adjustment (e.g., an AV interval extension, switching to a non-ventricular pacing mode) to encourage intrinsic activity of the heart during demand pacing. The ICI adjustment 71 circuit may be of the type as previously described that extends the AV interval from a base AV interval to an extended AV interval by adding to the base AV interval an AV interval extension. The AV interval extension may be a fixed programmable interval. The AV interval is extended after the time-out of a predetermined time period following the restoration of the AV interval from a previous AV interval extension. The AV interval extension is maintained for a set time or number of beats. Optionally, when a pacing pulse is issued, the AV interval may be restored back to the base AV interval (base ICI). The AV interval may be restored to the base AV interval in various circumstances.

When the AV interval is extended by the ICI adjustment circuit 71, the refractory circuit 73 in turn may extend the PVARP from a base PVARP value to an extended PVARP by adding a PVARP extension to the base PVARP. The PVARP extension may also be a fixed programmable interval. The extended PVARP is maintained until the AV interval is restored to the base AV interval value.

The device further includes a therapy control 75 that may be employed to initiate therapy for arrhythmic rhythms.

Figure 3A:
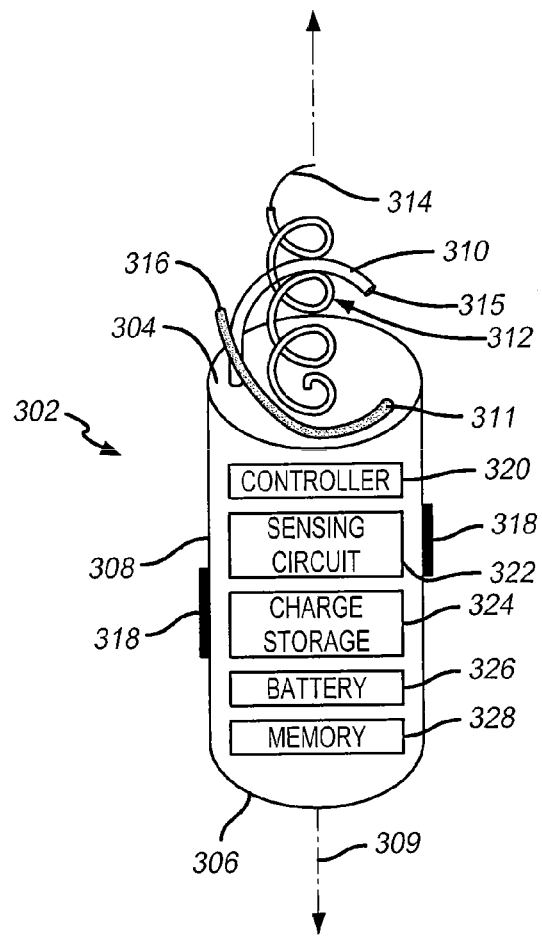
FIG. 3A illustrates a side perspective view of a LIMD in accordance with embodiments herein.
Figure 3B:
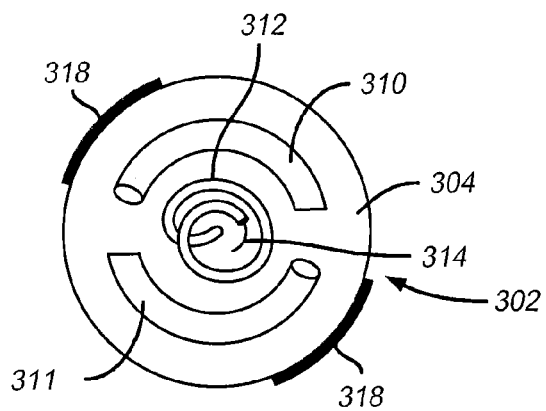
FIG. 3B illustrates an LIMD in accordance with embodiments herein.

FIGS. 3A and 3B illustrate an LIMD in more detail (such as from FIG. 1B). FIG. 3A illustrates a side perspective view of a LIMD 300 of oriented with the base 304 facing upward to illustrate electrodes 310-312 in more detail. FIG. 3B illustrates a bottom plan view of the LIMD 300. The LIMD 300 comprises a housing 302 having a proximal base 304, a distal top end 306, and an intermediate shell 308 extending between the proximal base 304 and the distal top end 306. The shell 308 is elongated and tubular in shape and extends along a longitudinal axis 309.

The base 304 includes one or more electrodes 310-312 securely affixed thereto and projected outward. For example, the outer electrodes 310, 311 may be formed as large semi-circular spikes or large gauge wires that wrap only partially about the inner electrode 312. The electrodes 310, 311 may be located on opposite sides of, and wound in a common direction with, the inner electrode 312. The first or outer electrodes 310, 311 are provided directly on the housing 302 of the LIMD 300 at a first position, namely at or proximate a periphery of the base 304 of the housing. The outer electrodes 310, 311 are positioned near the periphery of the base 304 such that, when the LIMD 300 is implanted in the local chamber (e.g., right atrium), the outer electrodes 310, 311 engage the local chamber wall tissue at tissue of interest for a local activation site that is near the surface of the wall tissue, and that is within the conduction network of the local chamber. The outer electrodes 310, 311 are physically separated or bifurcated from one another and have separate distal outer tips 315, 316. The outer electrodes 310, 311 are electrically joined to one another (i.e., common), but are electrically separated from the inner electrode 312.

The second or inner electrode 312 is also provided directly on the housing 302 of the LIMD 300 at a second position, namely at or proximate to a central portion of the base 304 of the housing. The inner electrode 312 is positioned near the center of the base 304 and is elongated such that, when the LIMD 300 is implanted in the local chamber, the inner electrode 312 extends a majority of the way through the wall tissue (e.g. septum) until reaching tissue of interest near the adjacent chamber wall. The inner electrode 312 is inserted to a depth such that a distal tip thereof is located at tissue of interest for an activation site that is physiologically coupled to wall tissue of the adjacent chamber (e.g. right ventricle). For example, the inner electrode 312 may extend until the distal tip extends at least partially through a septum to a position proximate to a distal wall tissue within the conduction network of the adjacent chamber. Optionally, the inner electrode 312 may be inserted at a desired angle until the distal end enters the ventricular vestibule. By located the distal tip of the inner electrode 312 at an adjacent chamber activation site, the inner electrode 312 initiates contraction at a distal activation site within the conduction network of the adjacent chamber without physically locating the LIMD 300 in the adjacent chamber. The inner and outer electrodes 310-312 may be formed as multiple cathode electrodes that are actively fixated to the myocardium. The outer cathode electrodes 310, 311 may be configured as screws with a large pitch (e.g. length between adjacent turns), large diameter and may have a length that is relatively short, while the inner electrode 312 is configured as a screw with a common or smaller pitch, small diameter and longer length. The screw shape of the outer electrodes 310, 311 is used to firmly adhere them to the cardiac tissue. The outer electrodes 310, 311 may have very little or no insulation material thereon to facilitate a good electrical connection to local wall tissue along the majority or the entire length of the outer electrodes 310, 311 for delivering stimulus pulses and sensing electrical activity in the local chamber where the LIMD 300 is located.

The inner electrode 312 is shaped in a helix or screw and is longer (e.g., extends a greater distance from the base) than the outer electrodes 310, 311. The inner electrode 312 is fashioned to an appropriate length that permits it to drill a predetermined distance into, or entirely through, the septum at the desired location. For example, the inner electrode 312 may be provided with a desired length sufficient to extend through, or to a desired distance into, a septum region separating two chambers of the heart.

The inner electrode 312 may be formed as a single conductive wire or a bundle of conductive wires, where a proximal portion of the wire is covered with insulation, while the distal tip 314 is covered with insulation and is exposed. By covering the proximal portion of the electrode 312 with insulation, this limits electrical conduction of the conductive wire to tissue surrounding the distal tip 314. When implanted, the distal tip 314 of the electrode is located far below the surface tissue of the chamber wall in which the LIMD 300 is located. As a consequence, the distal tip 314 of the inner electrode 312 directly engages or is located proximate to the surface tissue of an adjacent chamber wall. Hence, the distal tip will 314 senses electrical activity from the conductive network of the adjacent chamber that is representative of physiologic behavior (e.g., conduction pattern) of the adjacent chamber. Also, when delivering stimulus pulses, the distal tip 314 will deliver the pulses into the conductive network of the adjacent chamber wall.

Optionally, a single anode electrode or multiple anode electrodes 318 may be provided. The anode electrode(s) 318 may be located along one or more sides of the shell 308, and/or on the top end 306 of the LIMD 300.

The LIMD 300 includes a charge storage unit 324 and sensing circuit 322 within the housing 302. The sensing circuit 322 senses intrinsic activity, while the change storage unit 324 stores high or low energy amounts to be delivered in one or more stimulus pulses. The electrodes 310-312 may be used to deliver lower energy or high energy stimulus, such as pacing pulses, cardioverter pulse trains, defibrillation shocks and the like. The electrodes 310-312 may also be used to sense electrical activity, such as physiologic and pathologic behavior and events and provide sensed signals to the sensing circuit 322. The electrodes 310-312 are configured to be joined to an energy source, such as a charge storage unit 324. The electrodes 310-312 receive stimulus pulse(s) from the charge storage unit 324. The electrodes 310-312 may be the same or different size. The electrodes 310-312 are configured to deliver high or low energy stimulus pulses to the myocardium.

The LIMD 300 includes a controller 320, within the housing 302. The controller 320 includes one or more processors that execute program instructions stored in the memory 328 to perform in the operations described herein. The controller 320 causes the charge storage unit 324 to deliver activation pulses through each of the electrodes 310-312 in a synchronous manner, based on information from the sensing circuit 322, such that activation pulses delivered from the inner electrode 312 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 310-312 are spaced radially and longitudinally apart from one another such that the local activation site (e.g., right atrium) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g. AV delay).

The processor is responsive to execution of the program instructions. The processor adjusts the base ICI by an ICI adjustment, during one or more of the multiple cardiac cycles, to promote intrinsic heart activity. The processor further counts a number of the cardiac cycles in which the ICI adjustments occurred in conjunction with arrhythmias to identify an excessive adjustment count and modifies the ICI adjustment to utilize a new ICI adjustment based on the excessive adjustment count. The base ICI corresponse to at least one of an AV interval or PVARP interval and the ICI adjustment corresponds to at least one of an AV extension or a rate adaptive refractory reduction. The processor adjusts the base ICI by an ICI adjustment, during one or more of the multiple cardiac cycles, to promote intrinsic heart activity. The processor further counts a number of the cardiac cycles in which the ICI adjustments occurred in conjunction with arrhythmias to identify an excessive adjustment count and modifies the ICI adjustment to utilize a new ICI adjustment based on the excessive adjustment count. The adjust operation changes the base ICI utilizing different ICI adjustments during different corresponding cardiac cycles within the multiple cardiac cycles. Optionally, the processor further identifies the arrhythmias that are induced by extending the base ICI by the ICI adjustment in connection with AV extension. The processor identifies the arrhythmias that are induced by reducing the base ICI by the ICI adjustment in connection with rate adaptive refractory reduction. The processor measures intervals between ventricular and atrial events and identifies a select level of change within the intervals between the ventricular and atrial events. Optionally, the processor confirms when pacemaker-mediated-tachycardia (PMTS) occur and increments the excessive adjustment count for at least a portion of the PMTS. The modify operation includes reducing the ICI adjustment by a predetermined amount and includes changing the ICI adjustment to correspond to a prior ICI adjustment. The base ICI corresponds to at least one of a base AV interval or a post ventricular atrial refractory period (PVARP) interval.

Figure 4:
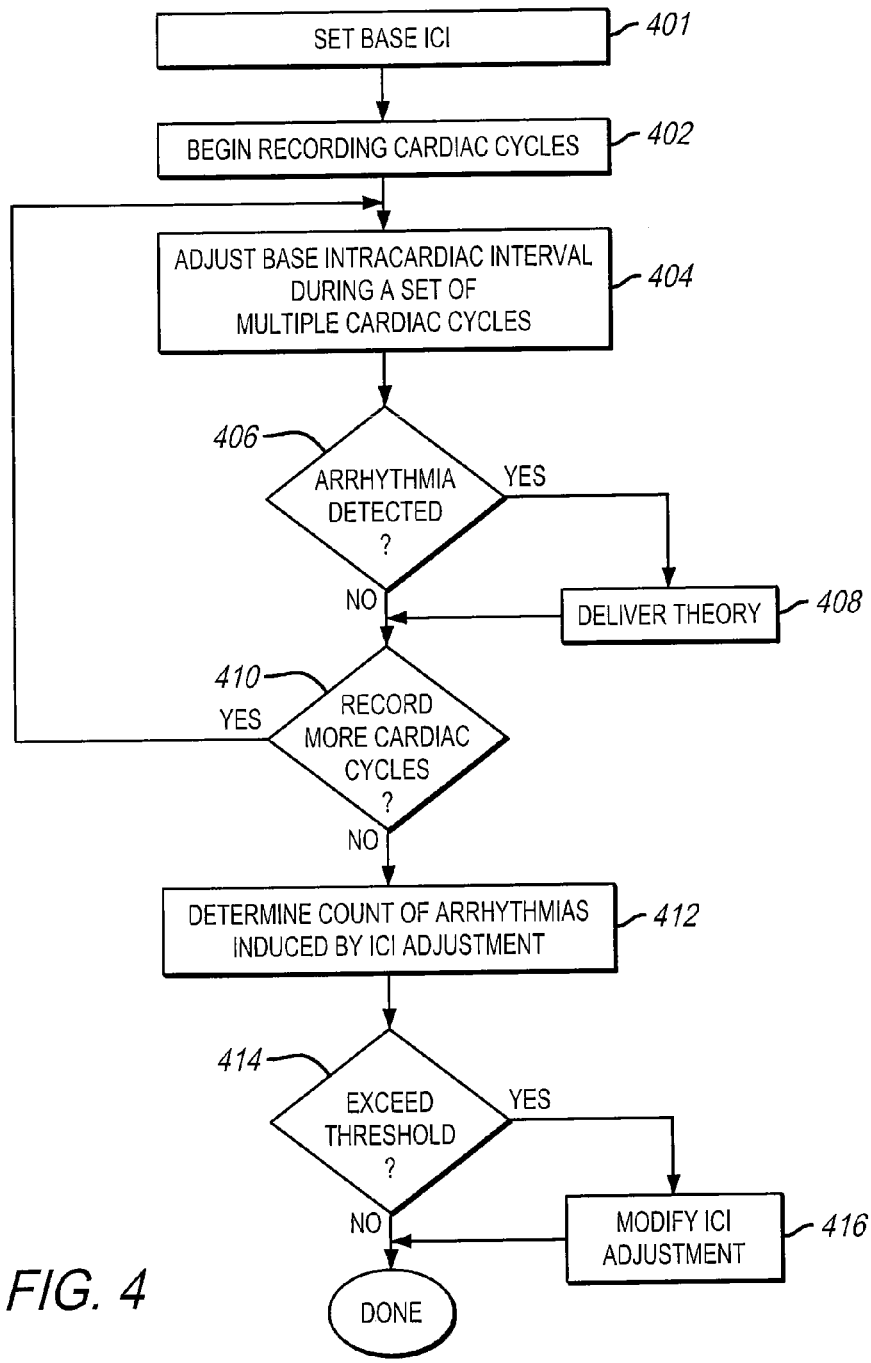
FIG. 4 illustrates a method for managing modifications to programmed intracardiac intervals in accordance with embodiments herein.

FIG. 4 illustrates a method for managing modifications to programmed intracardiac intervals in accordance with embodiments herein. The operations of FIG. 4 are carried out by the circuits, processors and program instructions stored in memory of the devices illustrated and described herein. Optionally, the operations of FIG. 4 may be performed continuously or alternatively only in connection with select modes of operation by the IMD. For example, the operations of FIG. 4 may be initiated when a select algorithm is enabled, such as the VIP algorithm, MVP algorithm, etc.

At 401, the timing control for a pulse generator circuit is programmed to deliver ventricular pacing pulses based on a base intracardiac interval (ICI). For example, the timing control 79 in FIG. 2 may be programmed with the base ICI. As a further example, the controller 320 (FIG. 3A) may be programmed with the base ICI (e.g. stored in memory).

At 402, the IMD begins to record cardiac signals over multiple cardiac cycles. The cardiac signals include intrinsic and/or paced atrial and ventricular events that are collected over multiple cardiac cycles. By way of example only, the number of cardiac events recorded at 404 may range between 5 and 50 cardiac events. The information regarding the cardiac signals may be recorded in various manners. For example, the raw sensed signals that are collected over one or more atrial sensing channel and one or more ventricular sensing channels may be stored in memory (e.g., memory 94 in FIG. 2 or Memory 328 in FIG. 3A). Additionally or alternatively, the sensed signals may be continuously analyzed for characteristics of interest with the characteristics of interest being recorded without the complete raw sensed signals necessarily being saved. As one example, a series of cardiac cycles may be analyzed to identify one or more characteristics of interest, such as, but not limited to, the AV interval/delay, the PVARP interval, the V-P interval, R-P interval, P-P interval, R-R interval and the like. The values for the characteristics of interest may be saved, with or without the underlying raw sensed signals from atrial and/or ventricular channels, in memory 94, 328.

At 404, while recording cardiac signals over multiple cardiac cycles, the method adjusts the base ICI by an ICI adjustment. By way of example only, the number of cardiac events recorded at 404 may range between 5 and 50 cardiac events. For example, the base ICI may be adjusted by the controller 60, 320. The base ICI is adjusted, for one or more of the multiple cardiac cycles to promote intrinsic heart activity. The base ICI may be adjusted once during collection of the set of cardiac cycles at 404. Alternatively, the base ICI may be collected more than once during collection of the set of cardiac cycles at 404. As explained hereafter, the base ICI may correspond to different characteristics of the cardiac cycle, such as the AV delay and/or the PVARP interval. Depending upon the characteristic corresponding to the base ICI, the ICI adjustment will vary. For example, when the base ICI corresponds to the AV delay, the ICI adjustment represents an AV extension to be added to the AV delay (as described below in more detail in connection with FIG. 5). As another example, when the base ICI corresponds to the PVARP interval, the ICI adjustment represents a rate adaptive refractory (RAR) reduction (as described below in more detail in connection with FIG. 6).

By way of example, the base ICI may be adjusted by a common amount during different sets of cardiac cycles. For example, once every 25 cardiac cycles, the base ICI may be modified by the ICI adjustment for one or more cardiac cycles. As another example the ICI adjustment may represent switching to a non-ventricular pacing mode. The ICI adjustment may be applied for one cardiac cycle out of each set of cardiac cycles. Alternatively, the ICI adjustment may be added to the base ICI for a sub-set of cardiac cycles out of each set of cardiac cycles. For example, the base ICI may be used for 15 out of 25 cardiac cycles and the base ICI plus the ICI adjustment may be used for 10 out of 25 cardiac cycles. The foregoing adjustment, may be repeated every 50 cardiac cycles during multiple iterations through 404-410.

The ICI adjustment may remain constant for a select number of iterations through the operations at 404-410. For example, the base ICI may be increased/decreased by a common amount every set of 50 cardiac cycles. Optionally, the adjustment may change the base ICI utilizing different ICI adjustments during different sets of cardiac cycles. For example, the operation at 404 may be repeated numerous times over a work-day period of time (e.g. 9-to-5), during which the controller 60, 320 records numerous sets of cardiac cycles. Over the course of the work day, the controller 60, 320 may adjust the based ICI periodically, such as by adding/subtracting a first ICI adjustment every 30-45 minutes. Additionally or alternatively, in the evening or while asleep, a second different ICI adjustment may be added/subtracted periodically. As an alternative example, the ICI adjustment may be repeatedly varied every few minutes, every half hour and the like, such as by incrementally increasing the ICI adjustment or incrementally decreasing the ICI adjustment between successive periods of time (or during successive sets of cardiac cycles), during which the cardiac cycles (and/or characteristics of interest) are recorded.

At 406, the method reviews the set of cardiac cycle(s) collected at 404 and determines whether an arrhythmia is detected. For example, when 50 cardiac cycles are collected at 404, the method analyzes various characteristics of interest from the 50 cardiac cycles to determine whether an arrhythmia occurred. For example, arrhythmia detector 62 or controller 320 identifies arrhythmias that occur in conjunction with extending the base ICI. When an arrhythmia occurs in conjunction with extension of the base ICI, the method designates the arrhythmia to be induced by extending the base ICI by the ICI adjustment. For example, the method may identify arrhythmias that are induced in connection with an AV extension, and/or a rate adaptive refractory reduction and/or switching to a non-ventricular pacing mode. As explained herein, the arrhythmia may be identified and declared as induced by the ICI extension based on various factors. When an arrhythmia is detected, flow moves to 408, at which a therapy is delivered to terminate the arrhythmia. Alternatively, at 406 when no arrhythmia is detected, flow moves to 410. At 410, the method determines whether cardiac signals for additional cardiac cycles are to be recorded. If so, flow returns to 404. Otherwise, flow advances to 412. The operations at 402-410 are repeated until cardiac signals are collected for a desired number of sets of cardiac cycles. For example, the operations at 404-410 may be repeated over multiple hours, days and/or another period of time until a desired amount of cardiac signal data is collected.

At 412, the method (e.g. controller 60 or controller 320) determines a count of the number of the cardiac cycles in which the ICI adjustments occurred in conjunction with arrhythmias referred to as an arrhythmia counter. The arrhythmia counters identify excessive adjustment count(s), in that an arrhythmia counter is incremented each time the ICI adjustment is followed by (or otherwise occurs in conjunction with) an arrhythmia. As explained hereafter in connection with FIGS. 5 and 6, more than one counter may be updated at 412.

At 414, the method (e.g. controller 60 or controller 320) determines whether one or more of the counters identified at 412 exceed a corresponding threshold. Various types of counters are described hereafter in connection with the embodiments of FIGS. 5 and 6, where such counters are compared to corresponding thresholds at 414. When one or more counters at 414 exceeds a corresponding threshold, flow moves to 416. Otherwise, the process of FIG. 4 completes.

At 416, the method (e.g. controller 64 controller 320) modifies the ICI adjustment to utilize a new ICI adjustment based on the arrhythmia counts. For example, the modifying operation may include reducing and ICI adjustment by a predetermined amount, such as when the ICI adjustment correspond to an AV extension. As a further example, the modifying operation may change the ICI adjustment to correspond to a prior ICI adjustment. For example, the method may maintain a table correlating each AV extension or RAR reduction with corresponding counter values (e.g. counters identifying the number of arrhythmias that occurred in connection with the corresponding AV extension or RAR reduction). When a current ICI adjustment is identified to occur in conjunction with an excessive number of arrhythmias, the method may analyze prior ICI adjustments and corresponding counts of physiologic behavior (e.g. arrhythmias). Based on the content of the table, the method may determine that few or no arrhythmias occurred in conjunction with the one or more prior AV extensions (or RAR reductions). By way of example, the method may choose a prior AV extension or RAR reduction that is closest in length to the current ICI adjustment that is associated with an excessive number of arrhythmias. The modified ICI adjustment is utilized to update the corresponding programmable parameters of the IMD during subsequent operations.

It is recognized that the operations of FIG. 4 may be carried out in various orders, as well as in parallel. For example, new cardiac signals may be recorded in connection with current cardiac cycles, while the counting operations at 412 are performed in parallel. Additionally or alternatively, the identifying operation 412 may be carried out following the arrhythmia detection at 406 and therapy delivery at 408, before the decision at 410 as to whether to record additional cardiac cycles. Additionally or alternatively, all of the operations at 412-416 may be carried out each iteration through 404-410.

Optionally, the operations of FIG. 4 may be carried out in connection with an IMD mode that switches to a non-ventricular pacing mode as the ICI adjustment.

As explained herein, the methods and devices repeat the operations of FIG. 4 continuously or periodically to count the number of ICI adjustments (e.g., VIP extension, MVP, switching to a non-ventricular pacing mode). The methods and devices identify sudden changes of the V-P or R-P interval and confirm when PMTS occur. For each PMT, an arrhythmia counter is incremented. When the arrhythmia counter exceeds a threshold, the methods and devise modify the ICI adjustment.

Figure 5:
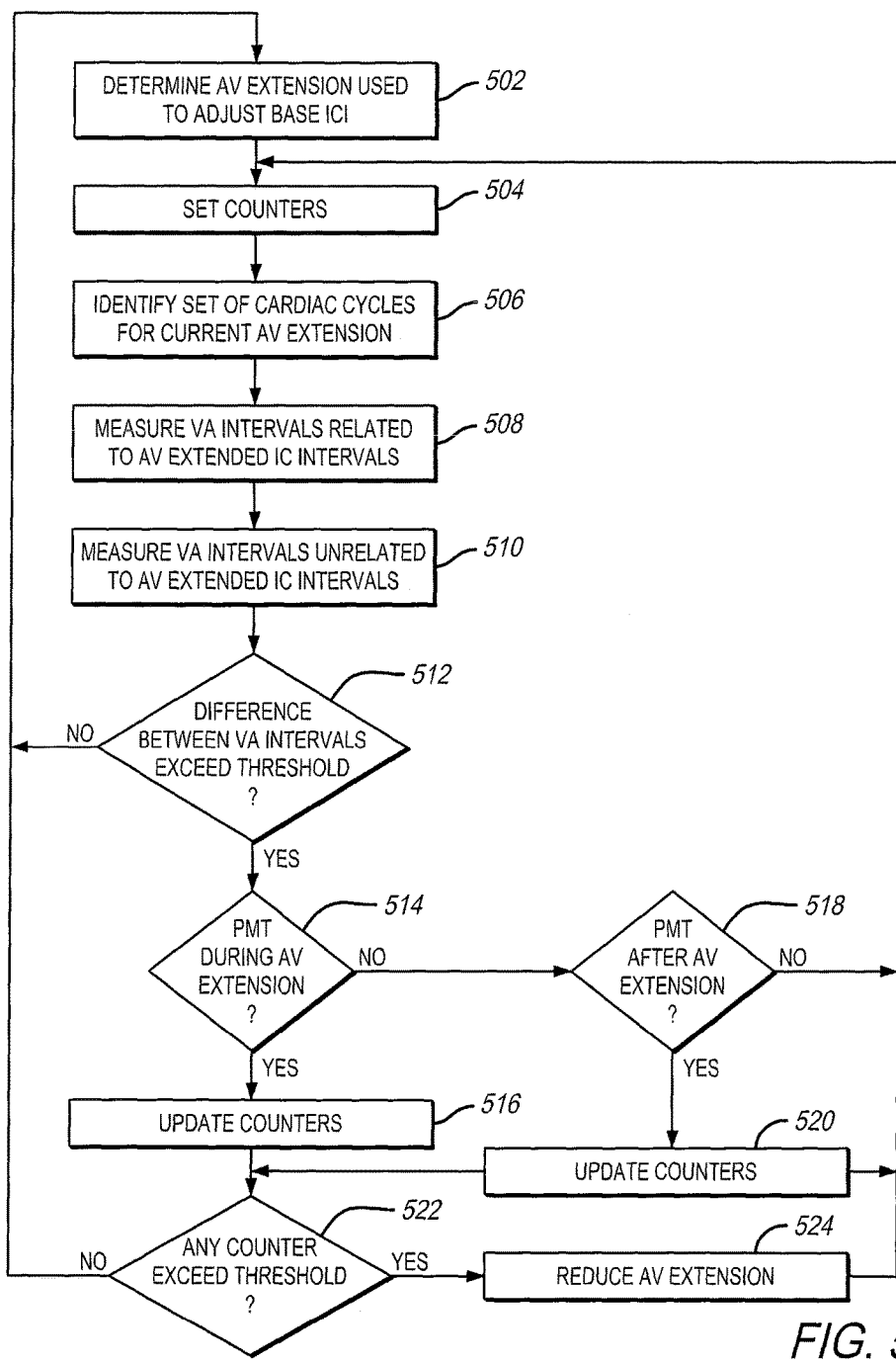
FIG. 5 illustrates a method for managing modifications to the AV interval in accordance with embodiments herein.
Figure 6:
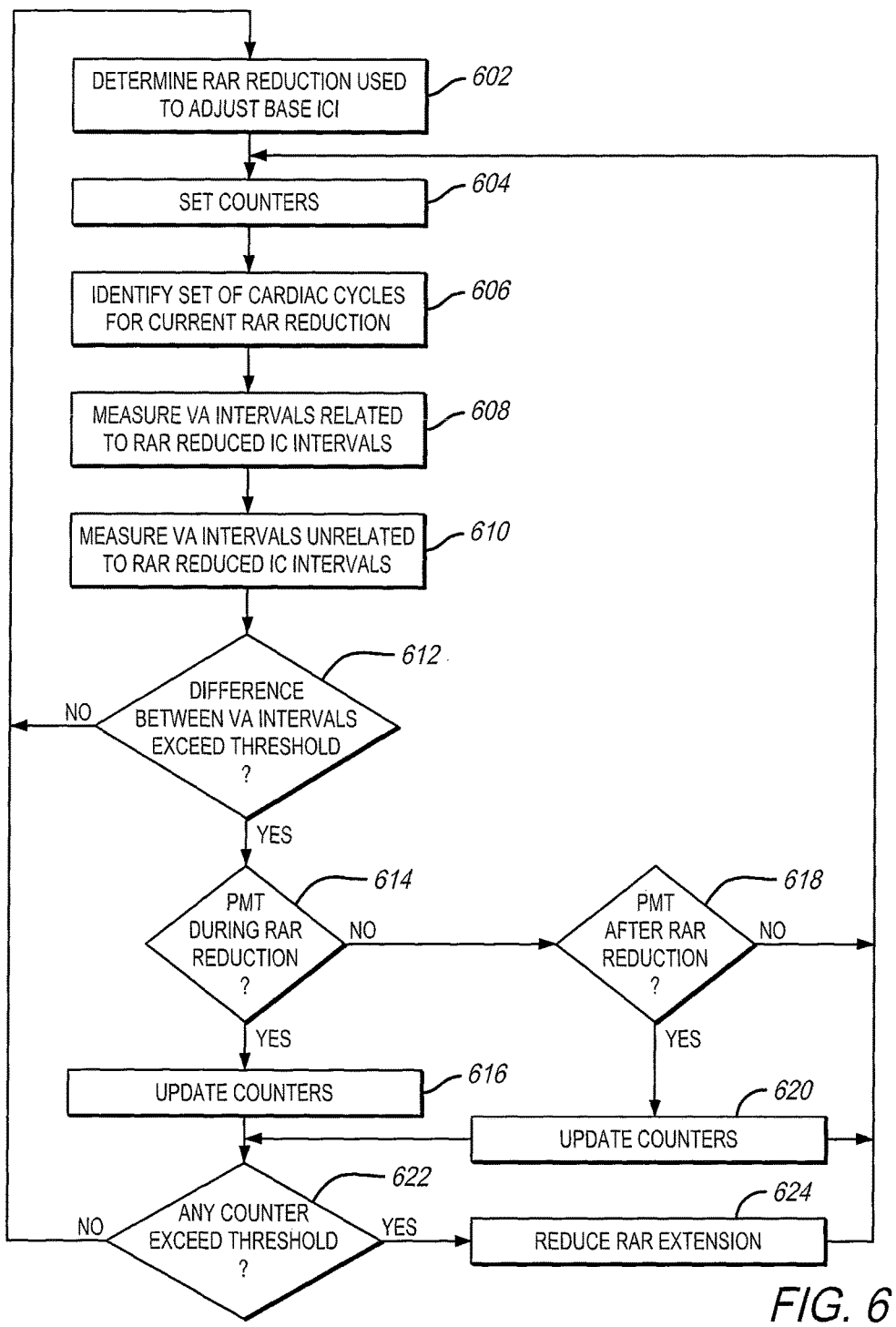
FIG. 6 illustrates a method for managing modifications to the PVARP in accordance with embodiments herein.

Optionally, the operation of FIGS. 4-6 may be modified to account for additional patient related parameters. For example, patient related parameters may represent activity, a circadian parameter, heart rate and the like. As one example, additional counters may be added to track activity, circadian parameters, heart rate or otherwise. By way of example, with reference to FIG. 5, a counter may be used to track the number of iterations with the operations of FIG. 5 for which the patient's heart rate is above a predetermined threshold. For example, it may be desirable to determine whether arrhythmias are occurring during ICI adjustments only in connection with an elevated heart rate or another patient related parameter. When it is determined that arrhythmias occur in conjunction with ICI adjustments for a particular patient related parameter, the modification to the ICI adjustment may be made only when the patient is experienced in the corresponding patient related parameter.

For example, the operations of FIGS. 4-6 may determine that, when a patient is exercising, if the ICI adjustment is applied, and arrhythmia may result. Accordingly, the methods and devices herein may determine to disable or reduce the amount of ICI adjustment when a patient is exercising. As another example, it may be determined that when a patient is sleeping, and an IMD (or LIMD) enters an MVP mode in which ventricular pacing is disabled, the patient may experience an excessive number of arrhythmias. Consequently, while a patient is sleeping, the MVP mode may be disabled or otherwise modified.

As a further example, it may be determined that when the AV interval is extended or an RAR interval is reduced during certain circadian conditions, that an excessive number of arrhythmias (PMT's) result. Consequently, during the corresponding circadian conditions, the IMD may reduce an amount to which the AV interval is extended, reduce the amount to which the RAR interval is reduced, disable such modes temporarily or take other appropriate corrective action as deemed appropriate in connection with the associated circadian condition.

FIG. 5 illustrates a method for managing modifications to the AV interval in accordance with embodiments herein. The operations of FIG. 5 are carried out by the circuits, processors and program instructions stored in memory of the devices illustrated and described herein. Optionally, the operations of FIG. 5 may be performed continuously or alternatively only in connection with select modes of operation by an IMD. For example, the operations of FIG. 5 may be initiated when a select algorithm is enabled, such as the VIP algorithm, MVP algorithm, or another algorithm that seeks to promote intrinsic physiologic behavior.

The operations of FIG. 5 are carried out relative to a preceding group of cardiac cycles, for which cardiac signals and/or characteristics of interest have been recorded and analyzed. For example, the operations of FIG. 5 may represent a more detailed explanation of at least one embodiment for implementing the operations at 412-416 in FIG. 4. Optionally, the operations of FIG. 5 may be performed in place of or in addition to the operations at 412-416 in FIG. 4.

At 502, one or more counters are set or initialized. The types of counters to be used are based on the nature of the intracardiac interval being modified. For example, when implemented in connection with AV extension, one counter represents an extend counter that tracks the number of times that an AV interval is extended by a corresponding amount. As explained hereafter, the counters are updated at 516 and 520. For example, when the extend counter is updated to equal 10 at 516 or 520, this is an indication that a corresponding AV extension (e.g., an extension of 100 msec.) was applied 10 times over a select period of time. Another counter, referred to as an incident counter, tracks the number of arrhythmias that occur in conjunction with extending the AV interval by the corresponding AV extension. To the extent that the arrhythmias are at least partially induced by extension of the AV interval, the incident counter represents a count of the number of times a particular AV extension length induced the arrhythmia. For example, the AV interval may be extended by a common AV extension (e.g. 100 ms) at 10 separate occasions over a period of time. Out of the 10 separate occasions in which the AV interval was extended, on 6 occasions an arrhythmia may have occurred in conjunction with the AV extension. In the foregoing example, the incident counter would be updated at 516 or 520 to equal 6 to indicate that arrhythmias were detected in conjunction with an AV extension of 100 ms.

At 504, a controller (e.g. controller 60 in FIG. 2 or controller 320 in FIG. 3A) identifies a set of cardiac cycles to be analyzed. The set of cardiac cycles may include and correspond to a single ICI event, namely one or more cardiac cycles preceding extension of the AV interval and one or more cardiac cycles following extension of the AV interval. The raw cardiac signals sensed over one or more atrial sensing channels and/or ventricular sensing channels may be accessed from memory (e.g. memory 94 in FIG. 2 or memory 328 in FIG. 3A). Additionally or alternatively, stored values for characteristics of interest for the set of cardiac cycles may be accessed from the memory.

At 506, the controller determines a current AV extension that was used by the IMD to adjust the base ICI during one or more of the cardiac cycles. In the present example, a single ICI event (e.g. AV extension) occurs during the set of cardiac cycles and thus a single AV extension is determined. For example, the AV extension may be stored in memory as a characteristic of interest with the cardiac signals for the set of associated cardiac cycles. Optionally, the controller may determine the current AV extension from programmed settings for the IMD as used in connection with a VIP algorithm, an MVP algorithm or other algorithm that modifies intracardiac intervals such as in connection with seeking to promote intrinsic physiologic behavior.

At 508, the controller analyzes characteristics of interest from one or more cardiac cycles that are related to extension of the AV interval (the ICI event). For example, the controller measures VA intervals between ventricular and atrial events of interest. The VA intervals may be between sensed or paced ventricular events and sensed or paced atrial events. For example, the VA interval may correspond to a ventricular paced event and an atrial paced event. As another example, the VA interval may correspond to a ventricular sensed event and an atrial paced event. As a further example, the VA interval may correspond to a ventricular sensed event and an atrial sensed event.

The controller may determine the cardiac cycles that are related to AV extension in various ways. For example, in connection with a set of 50 cardiac cycles, the AV interval may be extended during the $5^{th}$ to $15^{th}$ cardiac cycles in the set. Accordingly, at least the $5^{th}$ to $15^{th}$ cardiac cycles following the $26^{th}$ cardiac cycle would relate to the AV extension. As one example, a predetermined number of cardiac cycles (e.g. 10) during and following use of an AV extension may be declared to relate to the AV extended IC interval. Additionally or alternatively, other techniques may be utilized to identify cardiac cycles that are related to AV extension, such as based on the morphology of the cardiac signals collected, based on a mode of the IMD, and/or based on a predetermined time window beginning at the time that the AV extension is applied.

At 510, the controller analyzes characteristics of interest from one or more cardiac cycles that are unrelated to extension of the AV interval (the ICI event). For example, the controller 60, 320 measures VA intervals between ventricular and atrial events of interest. The VA intervals may be between sensed or paced ventricular events and sensed or paced atrial events. The controller 60, 320 may determine the cardiac cycles that are unrelated to AV extension in various ways. For example, in connection with a set of 50 cardiac cycles, the AV interval may be extended during the $5^{th}$ to 15th cardiac cycles. Accordingly, at least the first four cardiac cycles in the set of 50 cardiac cycles would be unrelated to AV extension. Optionally, all or a later portion of the cardiac cycles after the $15^{th}$ cardiac cycle may be unrelated to the AV extension. Additionally or alternatively, other techniques may be utilized to identify cardiac cycles that are unrelated to AV extension, such as based on the morphology of the cardiac signals collected, based on a mode of the IMD, based on a predetermined time window following use of an AV extension (e.g. X seconds or Y cardiac cycles after ceasing to use the AV extension).

At 512, the method determines a VA interval difference between i) the VA intervals related to the AV extended IC intervals and ii) the VA intervals unrelated to the AV extended IC intervals. The VA interval difference is compared to a threshold. When the VA interval difference does not exceed the threshold, the method determines that no or very little potential exists that an arrhythmia is occurring during the cardiac cycles related to the AV extended IC intervals. Consequently, the process returns to 502 and a new set of cardiac cycles are analyzed.

When the VA interval different exceeds the threshold, the potential exists that an arrhythmia is occurring during (and/or following) the cardiac cycles related to the AV extended IC intervals. Consequently, when the VA interval difference exceeds the threshold, flow moves to 514 where the method analyzes the cardiac cycles during the AV extension to determine, among other things, whether a pacemaker mediated tachycardia occurred during the AV extended period of time. For example, the arrhythmia detector 62 in FIG. 2 may perform the analysis at 514. Additionally or alternatively, the controller 320 in FIG. 3A may analyze the cardiac signals associated with one or more cardiac cycles to determine whether a PMT exists.

The operations at 514-520 account for the potential that a PMT may begin at different points in time. For example, a PMT may occur during an AV extension of the base ICI. Alternatively, a PMT may not initiate until after the IMD has ceased to use the AV extension. In the latter example, the PMT may initiate while the IMD is using the base ICI.

At 514, the method determines whether a PMT occurred during the AV extended IC interval. For example, an AV extended IC interval may be maintained for a subset of cardiac cycles. The subset of cardiac cycles may be analyzed, such as based on the morphology of the cardiac signals, timing of the characteristics of interest, and the like. When one or more PMT's is identified that occurs during the AV extended IC interval, flow moves to 516. Otherwise, flow moves to 518.

At 516, one or more appropriate counters are updated. For example, the method may increment a first arrhythmia counter associated with the present AV extension. The method may also increment an extension counter to maintain a running count of the number of times that the present AV extension was utilized.

At 518, the method determines whether a PMT occurred after completion of the AV extended IC interval. For example, an AV extended IC interval may be maintained for a subset of cardiac cycles and then terminated for a second subset of cardiac cycles. The second subset of cardiac cycles (during which the base ICI is utilized) may be analyzed, such as based on the morphology of the cardiac signals, timing of the characteristics of interest, and the like. When one or more PMT's is identified that occurs during the base ICI, flow moves to 520. Otherwise, flow returns to 504.

At 520, one or more appropriate counters are updated. For example, the method may increment a second arrhythmia counter associated with the present AV extension. The method may also increment the extension counter (e.g. the same extension counter as updated at 516) to maintain the running count of the number of times that the present AV extension was utilized.

In accordance with the foregoing, at 516 and 520, first and second arrhythmia counters are incremented each time a PMT is identified, either during an AV extension or after completion of an AV extension. Optionally, PMTs may initiate at other points in time, and as such, the operations at 514 and 518 may be modified accordingly to search for such PMTs.

At 522, the method (e.g. utilizing controller 64 controller 320) determines whether either of the first and second arrhythmia counters have been incremented to appoint that exceeds a corresponding threshold. When one or both of the first and second arrhythmia counters do not exceed corresponding thresholds, flow returns to 502 and the process of FIG. 5 is repeated for a new AV extension. Alternatively, at 522, when one or both of the first and second arrhythmia counters exceed corresponding thresholds, the potential exists that the present AV extension is excessive or otherwise undesirable. Accordingly, flow moves from 522 to 524.

At 524, the present AV extension is modified, such as by being reduced to a shorter AV extension to be used in subsequent operations. The AV extension may be reduced at 524 in various manners. For example, the AV extension may be reduced to a previously utilized AV extension that did not induce PMT's. Optionally, the AV extension may be reduced at 524 by a predetermined percentage or other set amount. Optionally, the AV extension may be reduced by an amount based upon the nature of the PMT identified. For example, when a PMT occurs during an AV extension (as identified at 514), the AV extension at 524 may be reduced by a first amount. When a PMT occurs after the AV extension (as identified at 518), the AV extension at 524 may be reduced by a second amount. Optionally, the AV extension may be reduced based upon a relation between the arrhythmia counters and the extension counters. For example, when the arrhythmia counters indicate that 1 arrhythmia occurred out of a large number of cardiac cycles for which AV extensions have been applied (as indicated by the extension counters), the degree to which the AV extension is reduced may be relatively small. Alternatively, when the arrhythmia a counters indicate that a large number of arrhythmias have occurred over a relatively small number of cardiac cycles for which AV extensions have been applied (as indicated by the extension counters), the degree to which the AV extension is reduced may be relatively large. After the adjustment of the AV extension at 524, flow returns to 504 where the new (reduced) AV extension is utilized during a desired number of subsequent cardiac cycles. Optionally, the reduction of the AV extension at 524 may be based in part upon one or more patient related parameters, such as patent activity, heart rate and/or circadian condition. For example, during exercise, the AV extension may be reduced by a greater amount, as compared to an amount of reduction in the AV extension when the patient is at rest. Optionally, when a patient is sleeping, the AV extension may be reduced by a first amount, and when a patient is awake the AV extension may be reduced by a different second amount.

FIG. 6 illustrates a method for managing modifications to the PVARP in accordance with embodiments herein. The operations of FIG. 6 are carried out by the circuits, processors and program instructions stored in memory of the devices illustrated and described herein. Optionally, the operations of FIG. 6 may be performed continuously or alternatively only in connection with select modes of operation by an IMD. For example, the operations of FIG. 6 may be initiated when a select algorithm is enabled, such as the VIP algorithm, MVP algorithm, or another algorithm that seeks to promote intrinsic physiologic behavior.

The operations of FIG. 6 are carried out relative to a preceding group of cardiac cycles, for which cardiac signals and/or characteristics of interest have been recorded and analyzed. For example, the operations of FIG. 6 may represent a more detailed explanation of at least one embodiment for implementing the operations at 412-416 in FIG. 4. Optionally, the operations of FIG. 6 may be performed in place of or in addition to the operations at 412-416 in FIG. 4.

At 602, one or more counters are set or initialized. The types of counters to be used are based on the nature of the intracardiac interval being modified. For example, when implemented in connection with RAR reduction, one counter represents a reduction counter that tracks the number of times that an PVARP is shortened by a corresponding amount. As explained hereafter, the counters are updated at 616 and 620. For example, when the reduction counter is updated to equal 5 at 616 or 620, this is an indication that a corresponding RAR reduction (e.g., a reduction of 100 msec.) was applied 5 times over a select period of time. Another counter, referred to as an incident counter, tracks the number of arrhythmias that occur in conjunction with shortening the PVARP by the corresponding RAR reduction. To the extent that the arrhythmias are at least partially induced by shortening of the PVARP, the incident counter represents a count of the number of times a particular RAR reduction length induced the arrhythmia. For example, the PVARP may be shortened by a common RAR reduction (e.g. 100 ms) at 10 separate occasions over a period of time. Out of the 10 separate occasions in which the PVARP was shortened, on 6 occasions an arrhythmia may have occurred in conjunction with the RAR reduction. In the foregoing example, the incident counter would be updated at 616 or 620 to equal 6 to indicate that arrhythmias were detected in conjunction with an RAR reduction of 100 ms.

At 604, a controller (e.g. controller 60 in FIG. 2 or controller 320 in FIG. 3A) identifies a set of cardiac cycles to be analyzed. The set of cardiac cycles may include and correspond to a single ICI event, namely one or more cardiac cycles preceding extension of the PVARP and one or more cardiac cycles following extension of the PVARP. The raw cardiac signals sensed over one or more atrial sensing channels and/or ventricular sensing channels may be accessed from memory (e.g. memory 94 in FIG. 2 or memory 328 in FIG. 3A). Additionally or alternatively, stored values for characteristics of interest for the set of cardiac cycles may be accessed from the memory.

At 606, the controller determines a current RAR reduction that was used by the IMD to adjust the base ICI during one or more of the cardiac cycles. In the present example, a single ICI event (e.g. RAR reduction) occurs during the set of cardiac cycles and thus a single RAR reduction is determined. For example, the RAR reduction may be stored in memory as a characteristic of interest with the cardiac signals for the set of associated cardiac cycles. Optionally, the controller may determine the current RAR reduction from programmed settings for the IMD as used in connection with a VIP algorithm, an MVP algorithm or other algorithm that modifies intracardiac intervals such as in connection with seeking to promote intrinsic physiologic behavior.

At 608, the controller analyzes characteristics of interest from one or more cardiac cycles that are related to extension of the PVARP (the ICI event). For example, the controller measures VA intervals between ventricular and atrial events of interest. The VA intervals may be between sensed or paced ventricular events and sensed or paced atrial events. For example, the VA interval may correspond to a ventricular paced event and an atrial paced event. As another example, the VA interval may correspond to a ventricular sensed event and an atrial paced event. As a further example, the VA interval may correspond to a ventricular sensed event and an atrial sensed event.

The controller may determine the cardiac cycles that are related to RAR reduction in various ways. For example, in connection with a set of 60 cardiac cycles, the PVARP may be shortened during the 26th cardiac cycles. Accordingly, one or more of the cardiac cycles following the 26$^{th}$ cardiac cycle would relate to the RAR reduction. As one example, a predetermined number of cardiac cycles (e.g. 10) during and following use of an RAR reduction may be declared to relate to the RAR reduced IC interval. Additionally or alternatively, other techniques may be utilized to identify cardiac cycles that are related to RAR reduction, such as based on the morphology of the cardiac signals collected, based on a mode of the IMD, and/or based on a predetermined time window beginning at the time that the RAR reduction is applied.

At 608, the controller analyzes characteristics of interest from one or more cardiac cycles that are unrelated to extension of the PVARP (the ICI event). For example, the controller measures VA intervals between ventricular and atrial events of interest. The VA intervals may be between sensed or paced ventricular events and sensed or paced atrial events. For example, the VA interval may correspond to a ventricular paced event and an atrial paced event. As another example, the VA interval may correspond to a ventricular sensed event and an atrial paced event. As a further example, the VA interval may correspond to a ventricular sensed event and an atrial sensed event.

The controller may determine the cardiac cycles that are unrelated to RAR reduction in various ways. For example, in connection with a set of 60 cardiac cycles, the PVARP may be shortened during the 26th cardiac cycles. Accordingly, at least the first 25 cardiac cycles in the set of 60 cardiac cycles would be unrelated to RAR reduction. Additionally or alternatively, other techniques may be utilized to identify cardiac cycles that are unrelated to RAR reduction, such as based on the morphology of the cardiac signals collected, based on a mode of the IMD, based on a predetermined time window following use of an RAR reduction (e.g. X seconds or Y cardiac cycles after ceasing to use the RAR reduction).

At 612, the method determines a VA interval difference between i) the VA intervals related to the RAR reduced IC intervals and ii) the VA intervals unrelated to the RAR reduced IC intervals. The VA interval difference is compared to a threshold. When the VA interval difference does not exceed the threshold, the method determines that no or very little potential exists that an arrhythmia is occurring during the cardiac cycles related to the RAR reduced IC intervals. Consequently, the process returns to 602 and a new set of cardiac cycles are analyzed.

When the VA interval different exceeds the threshold, the potential exists that an arrhythmia is occurring during (and/or following) the cardiac cycles related to the RAR reduced IC intervals. Consequently, when the VA interval difference exceeds the threshold, flow moves to 614 where the method analyzes the cardiac cycles during the RAR reduction to determine, among other things, whether a pacemaker mediated tachycardia occurred during the RAR reduced period of time. For example, the arrhythmia detector 62 in FIG. 2 may perform the analysis at 614. Additionally or alternatively, the controller 320 in FIG. 3A may analyze the cardiac signals associated with one or more cardiac cycles to determine whether a PMT exists.

The operations at 614-520 account for the potential that a PMT may begin at different points in time. For example, a PMT may occur during an RAR reduction of the base ICI. Alternatively, a PMT may not initiate until after the IMD has ceased to use the RAR reduction. In the latter example, the PMT may initiate while the IMD is using the base ICI.

At 614, the method determines whether a PMT occurred during the RAR reduced IC interval. For example, an RAR reduced IC interval may be maintained for a subset of cardiac cycles. The subset of cardiac cycles may be analyzed, such as based on the morphology of the cardiac signals, timing of the characteristics of interest, and the like. When one or more PMTs is identified that occurs during the RAR reduced IC interval, flow moves to 616. Otherwise, flow moves to 618.

At 616, one or more appropriate counters are updated. For example, the method may increment a first arrhythmia counter associated with the present RAR reduction. The method may also increment an extension counter to maintain a running count of the number of times that the present RAR reduction was utilized.

At 618, the method determines whether a PMT occurred after completion of the RAR reduced IC interval. For example, an RAR reduced IC interval may be maintained for a subset of cardiac cycles and then terminated for a second subset of cardiac cycles. The second subset of cardiac cycles (during which the base ICI is utilized) may be analyzed, such as based on the morphology of the cardiac signals, timing of the characteristics of interest, and the like. When one or more PMTs is identified that occurs during the base ICI, flow moves to 620. Otherwise, flow returns to 604.

At 620, one or more appropriate counters are updated. For example, the method may increment a second arrhythmia counter associated with the present RAR reduction. The method may also increment the extension counter (e.g. the same extension counter as updated at 616) to maintain the running count of the number of times that the present RAR reduction was utilized.

In accordance with the foregoing, at 616 and 620, first and second arrhythmia counters are incremented each time a PMT is identified, either during an RAR reduction or after completion of an RAR reduction. Optionally, PMTs may initiate at other points in time, and as such, the operations at 614 and 618 may be modified accordingly to search for such PMTs.

At 622, the method (e.g. utilizing controller 64 controller 320) determines whether either of the first and second arrhythmia counters have been incremented to appoint that exceeds a corresponding threshold. When one or both of the first and second arrhythmia counters do not exceed corresponding thresholds, flow returns to 602 and the process of FIG. 6 is repeated for a new RAR reduction. Alternatively, at 622, when one or both of the first and second arrhythmia counters exceed corresponding thresholds, the potential exists that the present RAR reduction is excessive or otherwise undesirable. Accordingly, flow moves from 622 to 624.

At 624, the present RAR reduction is modified, such as by being reduced to a shorter RAR reduction to be used in subsequent operations. The RAR reduction may be reduced at 624 in various manners. For example, the RAR reduction may be reduced to a previously utilized RAR reduction that did not induce PMTs. Optionally, the RAR reduction may be reduced at 624 by a predetermined percentage or other set amount. Optionally, the RAR reduction may be reduced by an amount based upon the nature of the PMT identified. For example, when a PMT occurs during an RAR reduction (as identified at 614), the RAR reduction at 624 may be reduced by a first amount. When a PMT occurs after the RAR reduction (as identified at 618), the RAR reduction at 624 may be reduced by a second amount. Optionally, the RAR reduction may be reduced based upon a relation between the arrhythmia counters and the extension counters. For example, when the arrhythmia counters indicate that 1 arrhythmia occurred out of a large number of cardiac cycles for which RAR reductions have been applied (as indicated by the extension counters), the degree to which the RAR reduction is reduced may be relatively small. Alternatively, when the arrhythmia a counters indicate that a large number of arrhythmias have occurred over a relatively small number of cardiac cycles for which RAR reductions have been applied (as indicated by the extension counters), the degree to which the RAR reduction is reduced may be relatively large. After the adjustment of the RAR reduction at 624, flow returns to 604 where the new (reduced) RAR reduction is utilized during a desired number of subsequent cardiac cycles.

Optionally, the reduction of the RAR reduction at 624 may be based in part upon one or more patient related parameters, such as patent activity, heart rate and/or circadian condition. For example, during exercise, the RAR reduction may be reduced by a greater amount, as compared to an amount of reduction in the RAR reduction when the patient is at rest. Optionally, when a patient is sleeping, the RAR reduction may be reduced by a first amount, and when a patient is awake the RAR reduction may be reduced by a different second amount.

Figure 7:
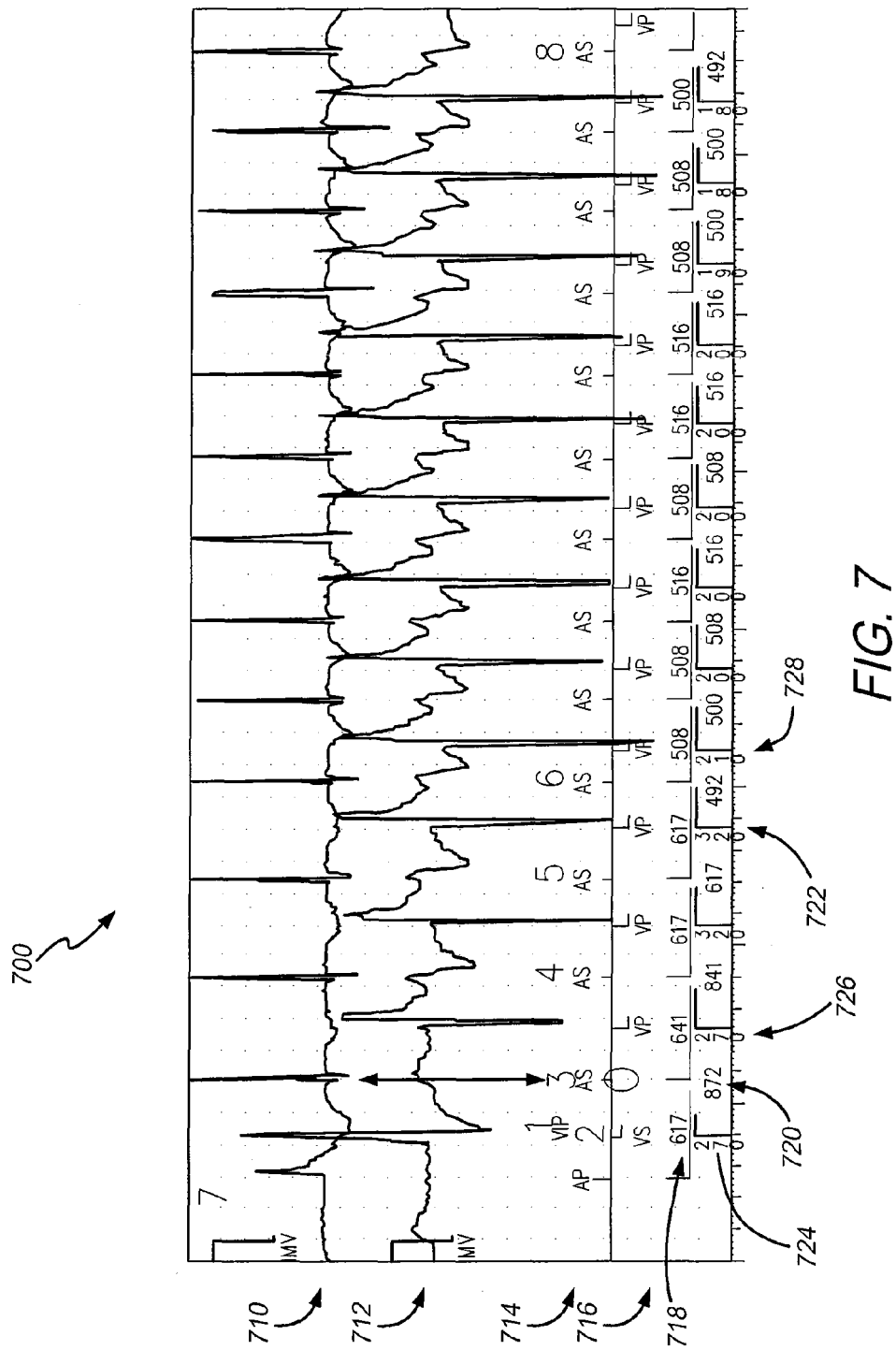
FIG. 7 illustrates a portion of a screenshot that includes examples of cardiac signals collected over multiple cardiac cycles in accordance with embodiments herein.

FIG. 7 illustrates a portion of a screenshot 700 that includes examples of cardiac signals (in which a PMT occurs) collected over multiple cardiac cycles in accordance with embodiments herein. The cardiac signals include an atrial sensing channel 710 and a ventricular sensing channel 712. The screenshot 700 also illustrate atrial markers 714 and ventricular markers 716. The atrial and ventricular markers indicate whether the atrial and ventricular sensing channels 710 and 712 detect paced or sensed events, where an atrial paced event is denoted as AP, an atrial sensed event is denoted as AS, a ventricular sensed event is denoted as VS and a ventricular paced event is denoted as VP. The screenshot 700 further indicates certain programmed intervals being utilized, such as the AA interval 718, VV interval 720, and the capital AV interval 722.

The screenshot 700 illustrates an example of an LIMD or IMD operating in connection with a VIP mode, in which the AV delay is extended during one or more of the cardiac cycles. By way of example, the atrial sensing channel 710 detected a paced atrial event AP at the marker denoted by reference numeral 7. The device is initially programmed with an AV delay of 270 ms, as denoted by the initial AV delay marker 724. The initial AV delay marker 724 corresponds to the base ICI. The device senses an intrinsic ventricular event as denoted by the marker VS (as denoted by reference 2). Following the ventricular sensed event VS at reference 2, an intrinsic atrial event is detected (as denoted at marker AS by reference 3). In accordance with the VIP mode, the device extends the AV delay to 320 as denoted at adjusted AV delay marker 726. By way of example, the AV delay may be extended during a VIP mode for 1 to 3 cardiac cycles. The adjusted AV delay marker 726 corresponds to the base ICI plus the ICI adjustment (e.g the base ICI of 270 plus the ICI adjustment of 50 ms). Following the ventricular sensed event at reference 2, an atrial sensed event occurs at reference 3, followed by a ventricular paced event VP, followed by another atrial sensed event AS at reference 4. Thereafter, a series of ventricular paced events VP are intermittent with a series of atrial sensed events AS (as partially denoted at reference 5 and reference). The cardiac signal from the atrial and ventricular sensing channels 710 and 712 are collected and analyzed.

The device (IMD or LIMD) operates in a rate tracking mode such that as the beat to beat rate increases during the PMT, after the cardiac cycles denoted at #4, #5, #6, the device reduces the AV delay to 210 ms (as denoted at marker 728). Thereafter, the AV delay is further reduced to 200, 190, 180 and the like as the device seeks to perform rate tracking during the PMT arrhythmia. At the reference 8, the device confirms that a PMT arrhythmia is occurring and will subsequently deliver a therapy to terminate the PMT.

In accordance with embodiments herein, the methods and devices collect and analyze the cardiac signals illustrated in FIG. 7. An arrhythmia counter is updated based on the PMT (e.g., incremented by 1). The example of FIG. 7 illustrates a portion of one set of cardiac cycles that are collected and analyzed (e.g. in connection with one iteration through the operations at 404-406 in FIG. 4). When the arrhythmia counter is incremented to a level that exceeds a corresponding threshold, the methods and devices adjust the ICI adjustment to be applied during subsequent VIP modes. For example, in the illustrated of FIG. 7, the ICI adjustment increased the AV delay up to 320 ms. When the arrhythmia counter exceeds the corresponding threshold, the ICI adjustment will be modified such that during subsequent VIP modes, the AV delay is adjusted to a duration less than 320 ms.

Figure 8A:
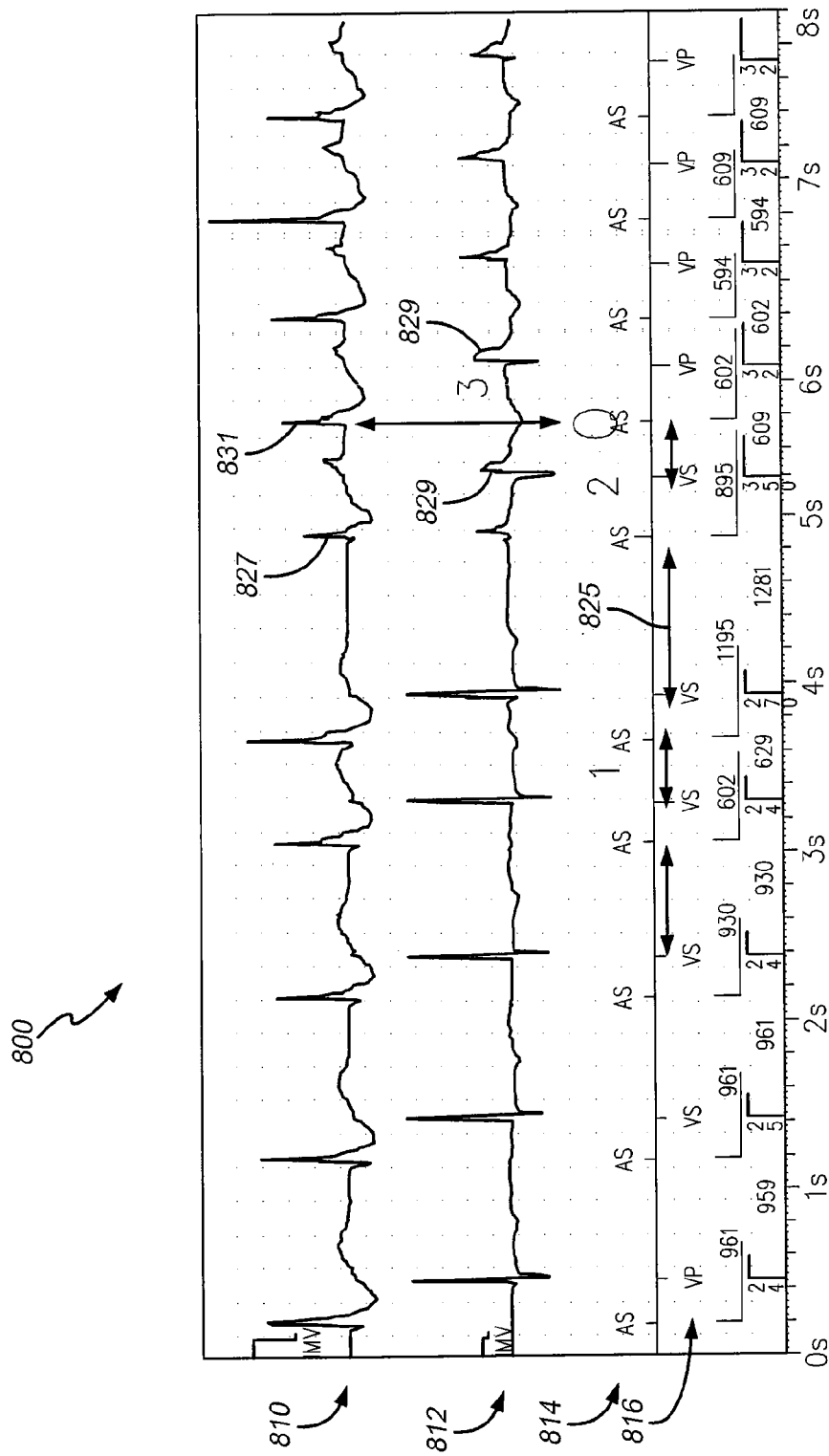
FIG. 8A illustrates a portion of a screenshot that includes examples of cardiac signals collected over multiple cardiac cycles in accordance with embodiments herein.
Figure 8B:
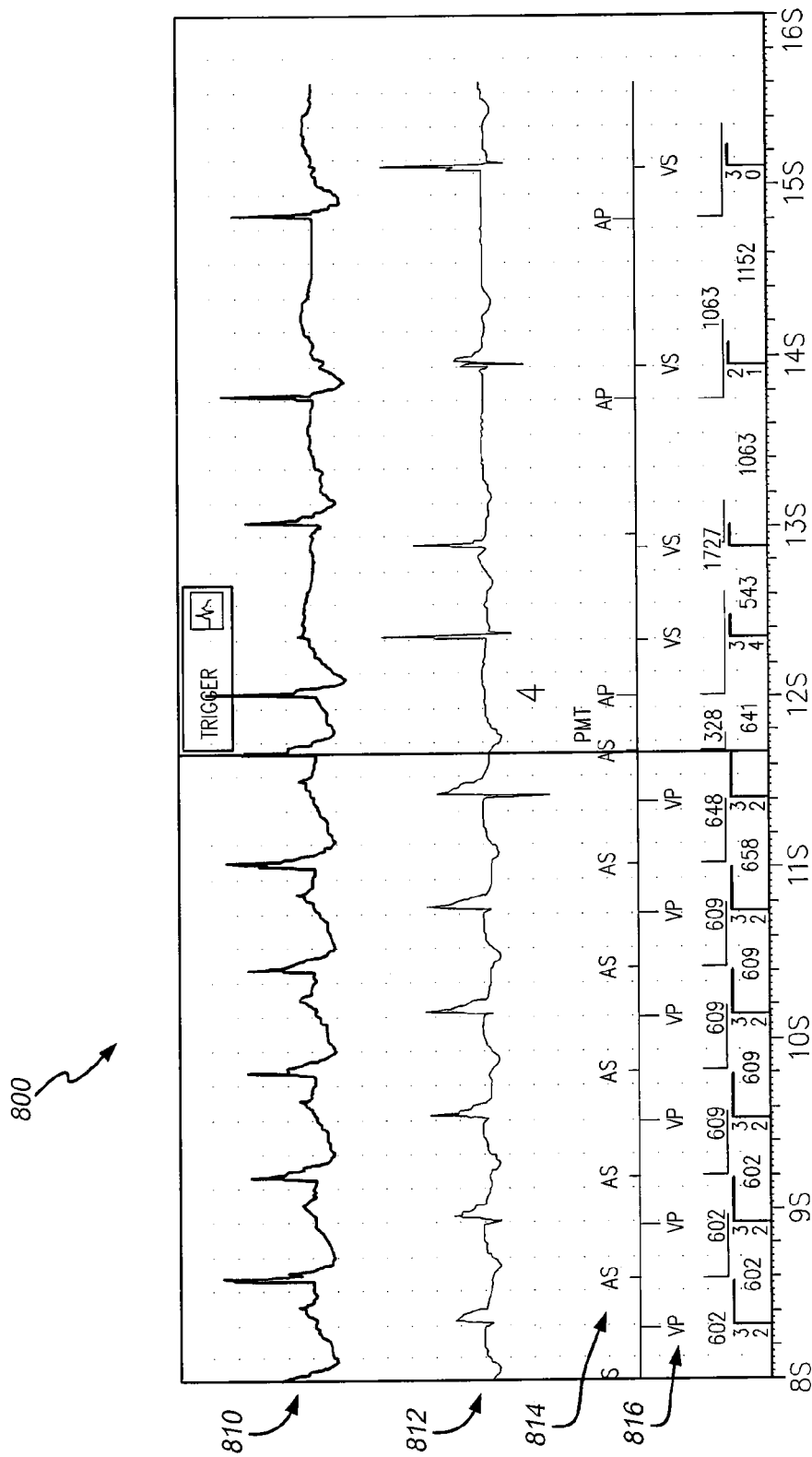
FIG. 8B illustrates a portion of a screenshot that includes examples of cardiac signals collected over multiple cardiac cycles in accordance with embodiments herein.

FIGS. 8A and 8B illustrate a portion of a screenshot 800 that includes examples of cardiac signals collected over multiple cardiac cycles in accordance with embodiments herein. The cardiac signals include an atrial sensing channel 810 and a ventricular sensing channel 812. The screenshot 800 also illustrate atrial markers 814 and ventricular markers 816. The atrial and ventricular markers indicate whether the atrial and ventricular sensing channels 810 and 812 detect paced or sensed events, where an atrial paced event is denoted as AP, an atrial sensed event is denoted as AS, a ventricular sensed event is denoted as VS and a ventricular paced event is denoted as VP. The screenshot 800 further indicates certain programmed intervals being utilized, such as the AA interval, VV interval, and the AV delay.

In the example of FIGS. 8A and 8B, the IMD or LIMD is utilizing a VIP extension as the ICI adjustment in order to allow the device start for atrial ventricular conduction. During the first few cardiac cycles, the patient exhibits physiologic behavior in which atrial events AS and ventricular events VS are sensed. In the region denoted at 825, the device adds and ICI adjustment to extend the AV interval from 270 ms to 350 seconds. Following extension of the AV interval at 825, the device begins to deliver an atrial paced event (AP) 827 followed by a ventricular paced event (VP) 829. Thereafter, a series of intrinsic atrial events are detected (AS) 831, followed by ventricular paced event (VP) 829. The intrinsic atrial events beginning at 831 (as denoted at marker 0) represent retrograde events that follow each paced ventricular event 829. The pattern of ventricular pacing (VP) and intrinsic atrial events (AS) represents a PMT that continues until the device identifies the PMT and begins delivering a corrective therapy at the marker denoted at reference 4 in FIG. 8B.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device, comprising:
a pulse generator circuit that times delivery of ventricular pacing pulses based on a base intracardiac interval (ICI);
a processor;
memory storing program instructions and storing atrial and ventricular events over multiple cardiac cycles; and
wherein, responsive to execution of the program instructions, the processor:
adjusts the base ICI by an ICI adjustment, during one or more of the multiple cardiac cycles, to promote intrinsic heart activity;
counts a number of the cardiac cycles in which the ICI adjustments occurred in conjunction with arrhythmias to identify an excessive adjustment count; and
modifies the ICI adjustment to utilize a new ICI adjustment based on the excessive adjustment count.

2. The device of claim 1, wherein the base ICI corresponds to at least one of an AV interval or a PVARP interval and the ICI adjustment corresponds to at least one of an AV extension or a rate adaptive refractory reduction.

3. The device of claim 1, wherein the adjust operation changes the base ICI utilizing different ICI adjustments during different corresponding cardiac cycles within the multiple cardiac cycles.

4. The device of claim 1, wherein the processor further identifies the arrhythmias that are induced by extending the base ICI by the ICI adjustment in connection with AV extension.

5. The device of claim 1, wherein the processor identifies the arrhythmias that are induced by reducing the base ICI by the ICI adjustment in connection with rate adaptive refractory reduction.

6. The device of claim 1, wherein the processor measures intervals between ventricular and atrial events and identifies a select level of change within the intervals between the ventricular and atrial events.

7. The device of claim 1, wherein the processor confirms when pacemaker-mediated-tachycardia (PMTs) occur and increments the excessive adjustment count for at least a portion of the PMTs.

8. The device of claim 1, wherein the modify operation includes reducing the ICI adjustment by a predetermined amount.

9. The device of claim 1, wherein the modify operation includes changing the ICI adjustment to correspond to a prior ICI adjustment.

10. The device of claim 1, wherein the base ICI corresponds to at least one of a base AV interval or a post ventricular atrial refractory period (PVARP) interval.

11. A method for managing modifications to intracardiac intervals, comprising:
timing a pulse generator circuit to deliver ventricular pacing pulses based on a base intracardiac interval (ICI);
storing atrial and ventricular events over multiple cardiac cycles; and
adjusting the base ICI by an ICI adjustment, during one or more of the multiple cardiac cycles, to promote intrinsic heart activity;
counting a number of the cardiac cycles in which the ICI adjustments occurred in conjunction with arrhythmias to identify an excessive adjustment count; and
modifying the ICI adjustment to utilize a new ICI adjustment based on the excessive adjustment count.

12. The method of claim 11, wherein the base ICI corresponds to at least one of an AV interval or a rate adaptive PVARP interval and the ICI adjustment corresponds to at least one of an AV extension or a rate adaptive refractory reduction.

13. The method of claim 11, wherein the adjusting operation changes the base ICI utilizing different ICI adjustments during different corresponding cardiac cycles within the multiple cardiac cycles.

14. The method of claim 11, further comprising identifying the arrhythmias that are induced by extending the base ICI by the ICI adjustment in connection with AV extension.

15. The method of claim 11, further comprising identifying the arrhythmias that are induced by reducing the base ICI by the ICI adjustment in connection with rate adaptive refractory adjustment.

16. The method of claim 11, further comprising measuring intervals between ventricular and atrial events and identifying a select level of change within the intervals between the ventricular and atrial events associated with an arrhythmia.

17. The method of claim 11, wherein the modifying operation includes reducing the ICI adjustment by a predetermined amount.

18. The method of claim 11, wherein the modifying operation includes changing the ICI adjustment to correspond to a prior ICI adjustment.

19. The method of claim 11, wherein the base ICI corresponds to at least one of a base AV interval or a post ventricular atrial refractory period (PVARP) interval.

20. The method of claim 11, further comprising delivering a corrective therapy from the pulse generator circuit.

* * * * *